US009731972B2

(12) United States Patent
Grigorian et al.

(10) Patent No.: US 9,731,972 B2
(45) Date of Patent: Aug. 15, 2017

(54) ARTICLE COMPRISING A COHESIVE CARBON ASSEMBLY

(71) Applicant: YAZAKI CORPORATION, Tokyo (JP)

(72) Inventors: Leonid Grigorian, Camarillo, CA (US); Sean Imtiaz Brahim, Camarillo, CA (US)

(73) Assignee: YAZAKI CORPORATION, Tokyo (JP)

( * ) Notice: Subject to any disclaimer, the term of this patent is extended or adjusted under 35 U.S.C. 154(b) by 0 days.

(21) Appl. No.: 14/824,968

(22) Filed: Aug. 12, 2015

(65) Prior Publication Data
US 2015/0344410 A1 Dec. 3, 2015

Related U.S. Application Data

(62) Division of application No. 13/572,514, filed on Aug. 10, 2012, now Pat. No. 9,136,536.
(Continued)

(51) Int. Cl.
C07C 233/00 (2006.01)
C01B 31/02 (2006.01)
(Continued)

(52) U.S. Cl.
CPC .......... C01B 31/0246 (2013.01); C07C 69/00 (2013.01); C07C 233/00 (2013.01);
(Continued)

(58) Field of Classification Search
None
See application file for complete search history.

(56) References Cited

U.S. PATENT DOCUMENTS 5,573,554 A * 11/1996 Fauteux .................. H01M 4/66
29/623.5
6,187,823 B1 2/2001 Haddon et al.
(Continued)

FOREIGN PATENT DOCUMENTS

WO WO-2012/033494 3/2012
WO WO-2010/102250 9/2012
WO WO-2012/177555 12/2012

OTHER PUBLICATIONS

Oswin (NL 128453) (Abstract) (1968).*
Non-Final Office Action dated Feb. 14, 2017 in U.S. Appl. No. 14/825,021.

Primary Examiner — Patrick Ryan
Assistant Examiner — Carmen Lyles-Irving
(74) Attorney, Agent, or Firm — Perkins Coie LLP; Viola T. Kung

(57) ABSTRACT

Cohesive carbon assemblies are prepared by obtaining a functionalized carbon starting material in the form of powder, particles, flakes, loose agglomerates, aqueous wet cake, or aqueous slurry, dispersing the carbon in water by mechanical agitation and/or refluxing, and substantially removing the water, typically by evaporation, whereby the cohesive assembly of carbon is formed. The method is suitable for preparing free-standing, monolithic assemblies of carbon nanotubes in the form of films, wafers, discs, fiber, or wire, having high carbon packing density and low electrical resistivity. The method is also suitable for preparing substrates coated with an adherent cohesive carbon assembly. The assemblies have various potential applications, such as electrodes or current collectors in electrochemical capacitors, fuel cells, and batteries, or as transparent conductors, conductive inks, pastes, and coatings.

22 Claims, 12 Drawing Sheets

Related U.S. Application Data

(60) Provisional application No. 61/523,125, filed on Aug. 12, 2011.

(51) Int. Cl.

| | | |
|---|---|---|
| *C07C 69/00* | (2006.01) | |
| *H01M 4/04* | (2006.01) | |
| *H01M 4/583* | (2010.01) | |
| *H01M 4/66* | (2006.01) | |
| *H01M 4/96* | (2006.01) | |
| *H01G 11/32* | (2013.01) | |
| *H01M 4/88* | (2006.01) | |
| *H01M 4/64* | (2006.01) | |
| *B82Y 30/00* | (2011.01) | |
| *B82Y 40/00* | (2011.01) | |

(52) U.S. Cl.
CPC .......... *H01G 11/32* (2013.01); *H01M 4/0402* (2013.01); *H01M 4/583* (2013.01); *H01M 4/663* (2013.01); *H01M 4/8825* (2013.01); *H01M 4/8875* (2013.01); *H01M 4/96* (2013.01); *B82Y 30/00* (2013.01); *B82Y 40/00* (2013.01); *C01B 2202/02* (2013.01); *C01B 2202/22* (2013.01); *H01M 4/64* (2013.01); *H01M 4/8807* (2013.01); *Y02E 60/13* (2013.01); *Y02E 60/50* (2013.01); *Y10T 428/26* (2015.01)

(56) References Cited

U.S. PATENT DOCUMENTS

| | | | |
|---|---|---|---|
| 6,440,598 B1 * | 8/2002 | Fukui | H01M 8/0204 29/623.5 |
| 6,855,398 B1 | 2/2005 | Machino et al. | |
| 7,938,987 B2 | 5/2011 | Grigorian et al. | |
| 2001/0010809 A1 | 8/2001 | Haddon et al. | |
| 2005/0106435 A1 | 5/2005 | Jang et al. | |
| 2008/0220334 A1 | 9/2008 | Inda | |
| 2009/0015984 A1 | 1/2009 | Grigorian et al. | |
| 2009/0116170 A1 | 5/2009 | Liu et al. | |
| 2009/0141428 A1 | 6/2009 | Roswech | |
| 2010/0159366 A1 | 6/2010 | Shao-Horn et al. | |
| 2010/0220074 A1 | 9/2010 | Irvin, Jr. et al. | |
| 2010/0330358 A1 | 12/2010 | Hashimoto et al. | |
| 2011/0143225 A1 * | 6/2011 | Nakagawa | H01M 4/8605 429/401 |
| 2012/0077080 A1 * | 3/2012 | Liu | H01G 11/06 429/206 |
| 2012/0295406 A1 | 11/2012 | Numata et al. | |
| 2013/0222975 A1 | 8/2013 | Yan et al. | |
| 2015/0344410 A1 | 12/2015 | Grigorian et al. | |

* cited by examiner

ARTICLE COMPRISING A COHESIVE CARBON ASSEMBLY

This application is a divisional of U.S. application Ser. No. 13/572,514, filed Aug. 10, 2012; which claims priority to U.S. Provisional Application No. 61/523,125, filed Aug. 12, 2011; the contents of the above identified applications are incorporated herein by reference in their entireties.

TECHNICAL FIELD

This invention relates to a cohesive assembly of carbon, and to methods for preparing a cohesive assembly of carbon, in which the starting carbon materials, under certain prescribed conditions, self-assemble into a disc, wafer, film, fiber, wire, or other object of a desired shape. In preferred embodiments, the carbon assembly prepared by the invented method comprises carbon nanotubes. The prepared assembly shows good mechanical strength and integrity, high carbon packing density, high surface area, and low electrical resistivity, and has various potential applications such as in electrical power storage and conductive coatings and films. The cohesive assembly of carbon is especially useful as an electrode or a current collector for an electrochemical capacitor, fuel cell, or battery. Furthermore, the method of making the assembly is environmentally friendly and cost-effective, as the raw materials consist of only the carbon starting material and water, with no toxic, corrosive, or otherwise harmful components.

BACKGROUND

Assemblies of carbon, derived from a variety of carbon sources, have a multitude of current and anticipated commercial, industrial, and high-technology applications. For example, activated charcoal or activated carbon, which is usually in the form of loose powder, particles, or irregular agglomerates, has a variety of uses in filtration and catalyst support. This material has also recently been applied to energy storage applications, as an ionic exchange medium or capacitor electrode material. Graphite in its various forms has numerous uses, for example, as refractory material, in brake linings, and as electrodes in electric arc furnaces. Intercalated graphite and expanded graphite have been studied for use as fire retardants and high temperature applications. These cohesive carbon assemblies have many desirable properties such as resistance to chemical attack, resistance to high temperatures, and high surface area in the case of activated carbon, and electrical conductivity and lubricity in the case of graphite. However, these materials typically require a binder or matrix material to form them into an assembly of a desired shape and size, having good mechanical strength and integrity.

More recently, assemblies of carbon nanotubes (CNTs) in various forms have attracted much attention and are being explored and developed for diverse applications. Such assemblies have been referred to in the literature as "buckypaper" or "buckydiscs". For example, Dharap et al in "Nanotube film based on single-wall carbon nanotubes for strain sensing", *Nanotechnology* 15 (2004), pp. 379-382, investigate the use of isotropic films of randomly oriented CNTs as mechanical strain sensors. Cao et al, in "Random networks and aligned arrays of single-walled carbon nanotubes for electronic device applications," *Nano Research* 1, 4 (2008), pp. 259-272, discuss the use of random networks or aligned arrays of CNTs as thin-film transistors. Ma et al, in "Methods of making carbide and oxycarbide containing catalysts," U.S. Pat. No. 7,576,027 B2, disclose catalyst supports for fluid phase chemical reactions made from randomly entangled CNT aggregates. And Liu et al, in "Electrochemical capacitor with carbon nanotubes," U.S. Patent Application Publication US 2009/0116171 A1, disclose electrolytic capacitors having electrodes made from free-standing CNT films.

Smalley et al in "Method for producing self-assembled objects comprising single-wall carbon nanotubes and compositions thereof," U.S. Pat. No. 7,048,999 B2, disclose CNT assemblies formed by a complex process of CNT end-cap removal and derivatization. The buckypaper disclosed therein is a loosely assembled CNT felt or mat that is supported on a substrate. Other structures disclosed therein such as molecular arrays and self-assembled monolayers are described as requiring a substrate or matrix material such as a resin, metal, ceramic, or cermet. Furthermore, the self-assembled structures disclosed therein comprise functional agents to bond the CNTs together, which may adversely affect the structures' electrical properties.

Tohji et al in "Carbon nanotubes aggregate, method for forming same, and biocompatible material," U.S. Patent Application Publication US 2007/0209093 A1, disclose a method for CNT aggregate formation involving exposure to fluorine gas followed by sintering at high temperature and pressure. The aggregates are characterized as being fragile.

Liu et al in US 2009/0116171 A1, and Hata et al in "Aligned carbon nanotube bulk aggregates, process for production of the same and uses thereof," U.S. Patent Application Publication US 2009/0272935 A1, disclose methods for preparing CNT assemblies that require the use of CNT forests grown by CVD processes on a substrate. These methods involve a sequence of solvent washing, pressing, and/or drying steps and are limited to the scale of the starting CNT forest. Furthermore, these assemblies are characterized by a predominant orientation or alignment of the CNTs, which imparts the assembly with anisotropic and largely unidirectional properties.

Whitby et al in "Geometric control and tunable pore size distribution of buckypaper and bucky discs," *Carbon* 46 (2008) pp. 949-956, disclose a frit compression method for forming CNT assemblies, which also requires high pressures. Also, the CNTs are not uniformly distributed within the assemblies, and the assemblies have large macropores and very high porosity (>80%).

A method to form a solution of single-walled CNTs in sulfuric super-acids is disclosed by Davis et al in "Phase Behavior and Rheology of SWNTs in Superacids," *Macromolecules* 37 (2004) pp. 154-160. A method is also disclosed to produce an entangled mat of CNT ropes by quenching in ether and filtering.

R. Signorelli et al in "High Energy and Power Density Nanotube Ultracapacitor Design, Modeling, Testing and Predicted Performance," presented at *The 19th International Seminar on Double Layer Capacitors and Hybrid Energy Storage Devices* (Dec. 7-9, 2009, Deerfield Beach, Fla., USA), and in "Electrochemical Double-Layer Capacitors Using Carbon Nanotube Electrode Structures," *Proceedings of the IEEE* 97, 11(2009), pp. 1837-1847, disclose vertically aligned single-walled CNT (SWCNT) and multi-walled CNT (MWCNT) "forest"-type assemblies intended for use as binder-free electrodes. These assemblies, however, show low bulk density of 0.45 g/cm$^3$ or less (0.1 g/cm$^3$ in the case of SWCNT), requiring an impractically high volume of material for adequate capacitor performance. Scalability of these CNT forests for manufacturing purposes is questionable, and they have inferior mechanical properties for use as current collectors.

A similar forest-type assembly produced from double-walled CNT (DWCNT), intended for use as a capacitor electrode, is disclosed by T. Asari in "Electric Double-Layer Capacitor Using Carbon Nanotubes Grown Directly on Aluminum", presented at *ICAC*2010, *The* 2010 *International Conference on Advanced Capacitors* (May 31-Jun. 2, 2010, Kyoto, Japan). This assembly has similar drawbacks as that of Signorelli; namely, low density, non-scalability, and inferior mechanical properties.

A. Izadi-Najafabadi et al, in "Extracting the Full Potential of Single-Walled Carbon Nanotubes as Durable Supercapacitor Electrodes Operable at 4 V with High Power and Energy Density," in *Advanced Materials*, n/a. doi: 10.1002/adma.200904349 (Published on-line Jun. 18, 2010), describe a capacitor electrode based on a high-purity SWCNT forest processed into a binder-free assembly. This assembly shows attractive electronic performance characteristics as an electrode when tested under laboratory conditions. However, a sealed capacitor device could not be produced using this assembly due to excessive swelling when impregnated with the liquid electrolyte, indicating that the assembly had inferior mechanical strength and integrity.

There is interest in applying CNT technology to electrochemical double-layer capacitors (EDLC), sometimes referred to as "supercapacitors" or "ultracapacitors". This capacitor type has power density somewhat lower than, but nearly approaching, that of standard capacitors, but much higher energy density, approaching that of standard batteries. EDLCs have many applications in consumer electronics, and are attractive for use in hybrid gas-electric vehicles and all-electric vehicles. Activated carbon is the most common material currently used as electrodes in EDLCs. However, its performance may be reaching its technological limit and materials capable of higher energy and power densities are desired, especially for vehicle applications.

Lithium-ion is one battery type of particular interest for application of carbon nanotubes. Modern Li-ion batteries typically comprise a carbon-based anode, a cathode comprising an oxide such as $LiCoO_2$, $LiFePO_4$, $LiNiCoAlO_2$, or the like, and an electrolyte comprising a lithium salt in an organic solvent. Li-ion batteries are commonly used in consumer electronics, and are attractive for use in hybrid gas-electric and all-electric vehicles. However, improvements in battery performance are needed for widespread vehicle application. Specifically, increased energy density, power density, lighter weight, and better reliability are desirable. Particularly attractive are thinner and/or lighter electrode materials having lower electrical resistance, more efficient ion transfer capability, and sufficient mechanical strength for battery use.

In a standard fuel cell, hydrogen is combined with oxygen to generate electric current and water as a by-product. One fuel cell type of current high interest is the proton exchange membrane or polymer electrolyte membrane (PEM) fuel cell. This design comprises a membrane electrode assembly (MEA), which in turn comprises a center proton exchange membrane (PEM), and an electrode on either side of the PEM. Each electrode comprises a catalyst layer and a gas diffusion layer (GDL). The catalyst layer is typically comprised of fine metal particles or powder (platinum for the anode, often nickel for the cathode) on a porous support material such as pressed carbon black. The GDL layer, which contacts the metallic current collector on the face opposite the catalyst layer, is usually comprised of carbon paper or carbon cloth. As in the case of Li-ion batteries, improvements in PEM fuel cell performance are also needed for widespread application, especially in vehicles. Stronger and more lightweight materials, having good electrical conductivity and providing more efficient electrochemical reactions, are desirable for use as electrode materials, as either the catalyst support and/or the GDL.

In various energy storage devices, including capacitors, fuel cells, and batteries, a current collector comprising a metal plate is typically attached to the exposed (outward-facing) surface of the electrode, to collect the current generated by the device and conduct it towards the machine or equipment that the device is powering. Aluminum and copper are typical metals used as current collectors. It is desirable that the weight and complexity of the energy storage devices be reduced, and one such approach is to combine the function of the electrode with that of the current collector in a single material. This may only be accomplished if both the conductivity and mechanical strength and integrity of the material are near enough to those of traditional current collectors, such that the performance of the device is not diminished. In fact, enhancement of the device performance by using a combined electrode/current collector would be ideal.

WO 2010/102250 discloses preparing cohesive carbon assembly by dispersing carbon in a liquid halogen (e.g. bromine), followed by substantial removal of the liquid. However, bromine is corrosive, highly toxic, environmentally harmful, and expensive.

Therefore, there exists a need for a method for preparing a cohesive carbon assembly that can avoid using the corrosive, toxic, and harmful halogen solvents, and provide a cost benefit.

SUMMARY OF THE INVENTION

The present invention is directed to a method of preparing a cohesive carbon assembly comprising: (a) obtaining a functionalized carbon starting material in a form of powder, particles, flakes, loose agglomerates, aqueous wet cake, or aqueous slurry; said functionalized carbon starting material is a carbon starting material which has been covalently or non-covalently functionalized such that it is dispersible in water; (b) dispersing the functionalized carbon starting material in an aqueous solution in a prescribed ratio to form a dispersion; and (c) substantially removing liquid from the dispersion in a controlled manner, whereby the cohesive carbon assembly is formed.

The present invention is also directed to a cohesive carbon assembly prepared by the method described above.

The present invention is further directed to applications of the cohesive carbon assembly in, e.g. electrical power storage and electromagnetic interference shielding. The cohesive carbon assembly may also be used as an electrode and/or a current collector in a capacitor, fuel cell, or battery.

DETAILED DESCRIPTION OF THE INVENTION

Figure 1:
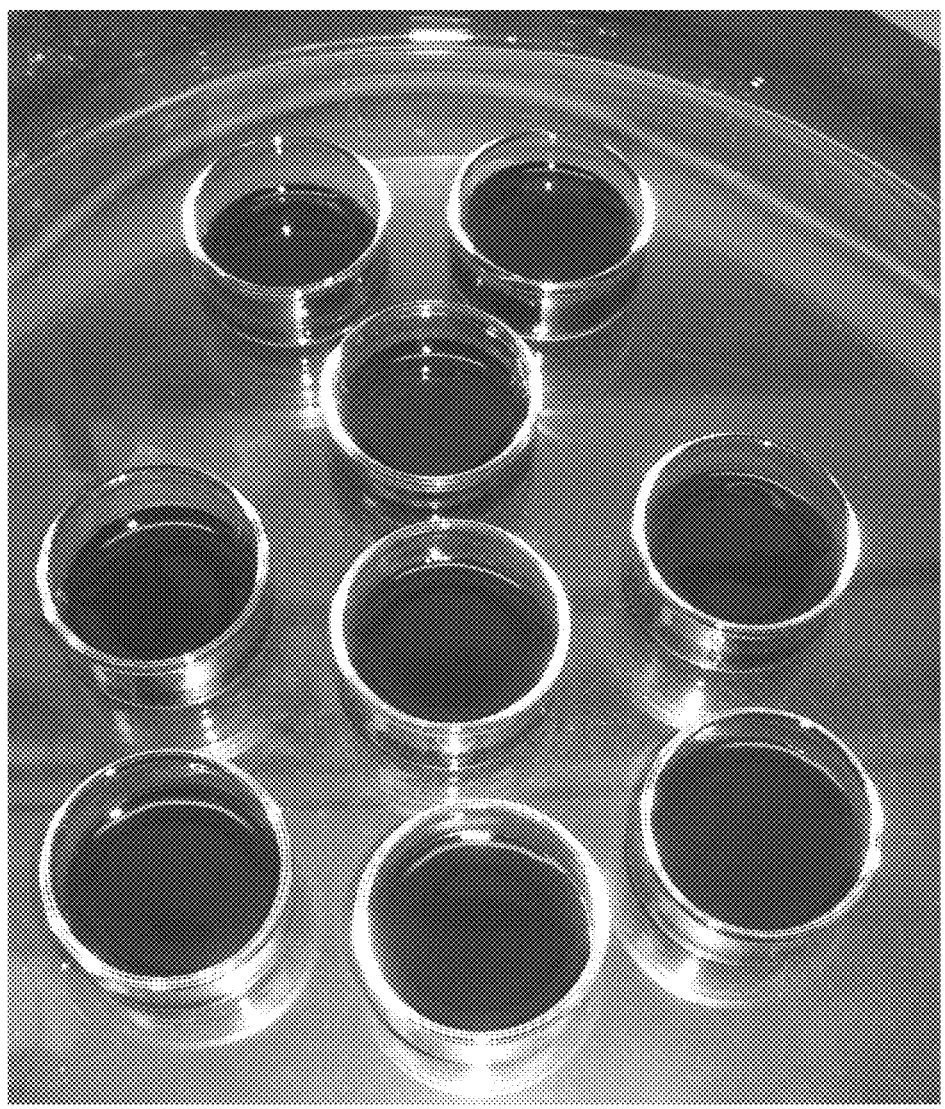
FIG. 1 is an optical image of nine aqueous CNT dispersions cast into glass dishes, with the water evaporating under ambient conditions, as described in Ex. 1.

One aspect of the invention relates to a method of preparing a cohesive carbon assembly. The method comprises: (a) obtaining a functionalized carbon starting material in a form of powder, particles, flakes, loose agglomerates, aqueous wet cake, or aqueous slurry; said functionalized carbon starting material is a carbon starting material which has been covalently or non-covalently functionalized such that it is dispersible in water; (b) dispersing the functionalized carbon starting material in an aqueous solution in a prescribed ratio to form a dispersion; and (c) substantially removing liquid from the dispersion in a controlled manner; whereby the cohesive carbon assembly is formed.

A cohesive assembly is defined herein as a self-assembled monolithic structure in which the carbon is uniformly distributed; the cohesive assembly has a distinct shape and size that is free-standing. The cohesive assembly is further defined in that it has sufficient mechanical strength and integrity that it does not require mechanical support by any other material, nor does it require the presence of a binder material to retain its strength, integrity, or functional properties. It also can be moved from place to place while retaining its structure, shape, and size.

The cohesive assembly is self-assembled in that, once the carbon in its initial form as described above is completely dispersed in a liquid medium, no additional chemical modifications, physical alterations, or mechanical forces are applied to the carbon in order to form the cohesive assembly.

The carbon starting material may comprise carbon nanotubes (CNTs) selected from the group consisting of single-walled carbon nanotubes (SWCNTs), double-walled carbon nanotubes (DWCNTs), multi-walled carbon nanotubes (MWCNTs), and any combination thereof. The carbon starting material may also comprise graphene, graphene oxide, graphite, expanded graphite, exfoliated graphite, amorphous carbon, and any combinations thereof. In one embodiment, the carbon starting material comprises SWCNTs. In another embodiment, the carbon starting material comprises DWCNTs. In a third embodiment, the carbon starting material comprises MWCNTs.

In one embodiment, the carbon starting material comprising CNTs is obtained in a form of powder, particles, flakes, loose agglomerates, aqueous wet cake, or aqueous slurry, or any appropriate forms that can be dispersed in water. In another embodiment, the carbon starting material may be ground, pulverized, or mechanically altered in one or more standard techniques to obtain the carbon starting material in an appropriate form before being dispersed in water.

A "functionalized carbon starting material", as used herein, refers to a carbon starting material that has been physically or chemically modified to contain one or more functional groups linked to the carbon either by covalent attachment or non-covalent attachment, such that the carbon starting material is dispersible in water. "Dispersible" is defined herein as, capable of being dissolved or dispersed in water to form a stable solution or suspension, at a concentration of at least 0.1 gram per gram of water. Typically, non-functionalized carbon starting materials are insoluble and non-dispersible in water (and many other liquids).

Carbon starting materials including CNTs, graphene, graphene oxide, and graphite may be functionalized by attaching one or more types of chemical functional groups to the carbon starting material. In the case of CNTs, this attachment may be to the walls and/or tube ends of the CNTs. This attachment may be achieved through physical or chemical processes. CNT starting materials may also be functionalized by depositing a substance or substances inside the tubes of the CNTs.

A preferable method of producing functionalized CNTs is to attach appropriate chemical functionalities onto the conjugated $sp^2$ carbon scaffold of the CNTs. One broad category of such functionalities includes polar groups that associate with water molecules through hydrogen bonding. Such derivatization of CNTs with polar moieties may be performed through covalent functionalization or non-covalent approaches.

Examples of covalent functionalization are attachment of acyl chloride (—COCl), hydroxyl (—OH), carboxyl (—COOH), or organic ester (—COOR) groups. Acyl chloride, hydroxyl, and carboxyl groups can be either the final terminal groups themselves, or may be used as precursor (intermediate) groups for subsequent attachment of other functional groups. For example, carboxylic acid-terminated CNT (—COOH) serves as the precursor for covalent attaching of a host of water-solubilizing polymers, dendrimers, oligomers, and proteins. Examples of functionalized CNT that proceed through the —COOH terminal group include polyethylene oxide (PEO)-functionalized CNT, polyethylene glycol (PEG)-functionalized CNT, polyvinyl acetate (PVA)-functionalized CNT, amino terminated polystyrene-functionalized CNT, and bovine serum albumin (BSA)-functionalized CNT.

Functional groups include, but are not limited to, carboxy, amide, hydroxy, glycol, ether, hemiacetal, hemiketal, amino, methacrylate, thiol, carbonyl, urethane, pyrrole, aniline, cyano, aminoacyl, acylamino, alkyl ester, and aryl ester. Carboxy, amide, hydroxyl, and glycol are preferred.

Examples of non-covalent functionalization are association with pyrene derivatives containing hydrophilic groups. The interaction in this case does not involve formation of covalent chemical bonds between functional groups on the CNT and the pyrene moiety. Instead, the non-covalent functionalization of CNT proceeds through Van der Waals π-π electronic interactions between the CNT side walls and the polyaromatic pyrene molecules. The presence of hydrophilic groups such as ammonium ions on the pyrene moieties then allow for CNT water dispersibility.

The degree of CNT functionalization is typically between about 0.01% and about 30% (as mole percentage of functional groups), preferably between about 0.05% and about 20%, more preferably between about 0.1% and about 10%, and yet more preferably between about 1.0% and 6.0%.

Functionalization of CNTs as described above may occur through methods or processes that are specifically intended to functionalize them, or as a side effect of processes applied to the CNTs for other purposes. For example, in industrial CNT manufacturing, treatment with strong acids such as HCl, $HNO_3$, and/or $H_2SO_4$ is often used to remove metallic and/or oxide impurities such as residual catalyst support and catalyst. This acid treatment may result in, for example, carboxylated or acid-sulfonated functionalized CNTs with high dispersibility in water. This may occur in the purification of SWCNT, DWCNT, or MWCNT, or any combination thereof. Use of intentionally or unintentionally functionalized CNTs, or both, as SWCNT, DWCNT, MWCNT, or any combination thereof, is within the scope of the present invention.

Functionalized CNTs are also commercially available. Examples include single-walled carbon nanotubes sold by Carbon Solutions Inc., Riverside, Calif. under the product grades P3 (1-3 atomic percent carboxy functionalized), P7 (PEG-derivatized, between approximately 5 and 20 wt %), P8 (m-polyaminobenzene sulfonic acid (PABS)-derivatized, between approximately 50 and 65 wt %), and P9 (between approximately 0.5 and 5.0 atomic percent amide group functionalized).

Baytubes® C 150 P multi-walled CNT, available from Bayer MaterialScience (Leverkusen, Germany), is an example of a commercial MWCNT product that is functionalized as a side effect of a process applied for another purpose. Through acid purification, likely performed using nitric acid, sulfuric acid, or a combination thereof, the MWCNT may be terminated with carboxylic acid (—COOH), hydroxy (—OH), or both functional groups, making the material dispersible in an aqueous medium. The degree of functionalization is estimated to be about 0.1-0.5 atomic percent.

The functionalized CNTs may supplied in the form of wetcake (loose agglomerates in a liquid), as a slurry, as a dispersion in water, or as dry particles. The wetcake material may be dried by any standard method, then mechanically broken apart into particles or loose agglomerates, and then used in the preparation of the cohesive carbon assemblies. Optionally the dried wetcake material may be further ground into smaller particles or powder, and then used in the preparation of the cohesive carbon assemblies. The wetcake, slurry, or dispersion may be used in preparation of the assemblies in the as-received condition, or it may be dried and optionally mechanically broken apart before use. The dry particles, which are typically smaller than 5 mm in the largest dimension, may be used as-received in the preparation of the cohesive carbon assemblies. Optionally, this material may be ground into smaller particles or powder and then used in the preparation of the cohesive carbon assemblies. Generally speaking, the powder, particles, flakes, or loose agglomerates of carbon used in the invented method are smaller than 1 cm in the largest dimension, preferably smaller than 3 mm in the largest dimension, and more preferably smaller than 1 mm in the largest dimension.

The aqueous solution used in the method of the invention may comprise any kind of water, including tap water, bottled water, distilled water, de-ionized water, $D_2O$, or any combination of these. In one embodiment, the aqueous solution is water, preferably it is at least 90% pure, or 95% pure, or 99% pure. In another embodiment, the aqueous solution contains dissolved ions or salts at a concentration of up to 20 weight percent in water. The aqueous solution may be acidic, alkaline, or neutral, and may have a pH anywhere within the range of about 1.5 to 14.0. A buffer may be added to the aqueous solution at a concentration of up to 10 weight percent.

In one embodiment, the aqueous solution does not contain any organic solvent. In another embodiment, a small amount of organic solvent, such as ethanol, 2-propanol, acetone, and the like, may be present in the aqueous solution. Up to about 5 weight percent of organic solvent may be added. If the amount of organic solvent is higher than this, the advantage of being environmentally friendly is lost, because upon evaporation a large amount of organic solvent may be released to the atmosphere, unless proper equipment is used to recover the liquid. Also, any waste solution generated in the process would need to be handled for disposal as an organic liquid, a hazardous material. Furthermore, the volatility of the dispersing solution may rise as the quantity of organic solvent is increased, making the process of evaporating the dispersing liquid unpredictable and difficult to control.

In step (b), the carbon starting material is dispersed in the aqueous solution, in a prescribed ratio. A prescribed ratio of a carbon starting material to the aqueous solution is defined as a ratio that will result in dispersion of the carbon in the aqueous solution, and in the formation of the cohesive assembly when liquid is removed. For a particular type of carbon starting material, there is a range of prescribed ratios that are determined experimentally. Within that range of prescribed ratios, that type of carbon starting material will disperse in the aqueous solution and can form a cohesive assembly when liquid is removed in a controlled manner.

If the ratios of the carbon starting material and aqueous solution (or "solution") amounts are outside the range of the prescribed ratios for that particular type of carbon starting material, a cohesive carbon assembly will not form. For example, if the ratio of the carbon starting material to solution is too high, the carbon starting material may not disperse completely in the solution, but rather remain as powder, particles, flakes, or loose agglomerates, which may appear floating or suspended in the solution, or settle to the bottom of the solution in the container. If the ratio of carbon starting material to solution is too low, the carbon starting material may disperse completely. It may then form into an assembly during removal of liquid, but then break into pieces at the end of the process. Or, the dispersed carbon may assemble into particles or flakes, but not into a monolithic cohesive assembly. Or, the dispersed carbon may simply remain as a residue of powder, particles, flakes, or loose agglomerates in the container when liquid is removed.

In one embodiment, the prescribed ratio of the carbon starting material to solution may be between about 0.015 and about 200 mg per gram of solution, between about 0.01 and about 50 mg per gram of solution, between about 0.05 and about 50 mg per gram of solution, between about 0.1 and about 30 mg per gram of solution, or between about 0.3 and about 10 mg per gram of solution. "About", as used herein, refers to +/−10% of the recited value.

In one embodiment, the carbon starting material comprising functionalized SWCNTs is dispersed in the solution in a prescribed ratio of between about 0.1 and about 20 mg carbon starting material per gram of solution.

Dispersing, as used herein, is forming a stable suspension of carbon in the solution. A stable suspension is one in which no visible powder, particles, flakes, or loose agglomerates precipitate out of the solution or settle to the bottom of the mixture when no mechanical agitation is applied. In one embodiment, to disperse the carbon in the solution, the carbon is first combined with the solution in a container to form a mixture, and then the mixture is mechanically agitated by one or more standard methods, for example, without limitation, mechanical stirring, and/or sonication (bath sonication, probe sonication, or a combination of the two), and/or microfluidization. In another embodiment, the carbon is first combined with the solution in a container to form a mixture, then the mixture is simultaneously mechanically agitated and refluxed at or near the solution boiling temperature for between 0.1 and 20 hours, preferably between 1 and 6 hours, and then the mixture is mechanically agitated by sonication and/or microfluidization.

Dispersion of the carbon starting material in the solution in step (b) may be carried out at a suitable temperature under a suitable pressure wherein the solution is in a liquid form, i.e. above the melting point and up to and including the boiling point of the solution under a suitable pressure. In one embodiment, the carbon starting material is dispersed in the solution at atmospheric pressure, at a temperature above about 0° C. and up to about 100° C., between ambient room temperature and about 45° C., or between 10° C. and 30° C. Ambient room temperature (about 20° C.) and pressure are typically suitable conditions. In another embodiment, the carbon starting material is dispersed in the solution at about 100° C. by refluxing.

Dispersion of the carbon starting material in the solution may be carried out in the presence of one or more types of mechanical agitation. The dispersion step may comprise more than one periods of mechanical agitation. In each period, one or more types of mechanical agitation may be carried out. The same type of mechanical agitation carried out at different periods may have the same or different parameters. In one embodiment, the dispersion of carbon starting material in the solution comprises two periods of mechanical agitation, the first period comprising sonication and the second period comprising microfluidization. In another embodiment, the dispersion of carbon in the solution comprises two periods of mechanical agitation, the first period comprising mechanical stirring and the second period comprising microfluidization.

Mechanical agitation may be carried out using standard laboratory magnetic stirring plate and magnetic stir bars immersed in the mixture of carbon and solution. Alternatively, mechanical agitation may be carried out using a high shear mixer comprising a rotor or impeller, together with a stationary component known as a stator, or an array of rotors and stators. The mixer is used in a tank containing the carbon starting material and the solution mixture to be mixed or in a pipe through which the mixture passes, to create shear.

Microfluidization may be carried out using commercially available equipment, for example, that produced by Microfluidics Corp., Newton, Mass.

Sonication may be carried out by a variety of methods using commercially available equipment, examples include, without limitation, an ultrasonic processor with a probe or wand, and an ultrasonic bath or tank. Sonication may be carried out for a suitable time period at a suitable energy level at a suitable temperature. In one embodiment, the suitable time period is between about 1 minute and about 100 hours, between about 5 minutes and about 5 hours, or about 20 minutes. The suitable energy level is at least 0.01 watt/gram of solvent, or between 0.16 watt/gram of solvent and about 1.6 watt/gram of solvent. The suitable temperature is the same as described supra.

The dispersion of carbon starting material in the solution in step (b) is different from commonly known methods of carbon dispersion, and in particular, CNT dispersion, in that no surfactant chemicals are needed to disperse the carbon starting material. In one embodiment, the carbon starting material is dispersed in the solution substantially free of surfactants. Surfactants are typically used to disperse carbon, and more specifically, carbon nanotubes, in a liquid, and in known methods of preparing carbon assemblies, surfactants are usually present as a residue. Examples of such surfactants include but are not limited to cetyl trimethylammonium bromide (CTAB), dodecylbenzenesulfonic acid sodium salt (NaDDBS), sodium cholate, sodium dodecyl sulphate (SDS), polyoxyethylene (10) octylphenol (Triton X-100) and poly(ethylene oxide) (20) sorbitan mono-oleate (Tween 80). "Substantially free of surfactants," as used herein, means less than 10%, preferably less than 1%, and more preferably less than 0.1% (w/w) of surfactants is present relative to the weight of carbon starting material used to prepare the assembly. Such surfactants are not needed to disperse the carbon in the solution, when the carbon is dispersed in a solution according to the method of the invention.

Typically, ionic surfactants such as cetyl trimethylammonium bromide (CTAB), dodecylbenzenesulfonic acid sodium salt (NaDDBS), sodium cholate, and sodium dodecyl sulphate (SDS), or nonionic surfactants such as polyoxyethylene (10) octylphenol (Triton X-100, Dow Chemical Co.) and poly(ethylene oxide) (20) sorbitan mono-oleate (Tween 80, ICI Americas, Inc.) are needed to effectively disperse CNTs in a liquid medium. These surfactants, when used to disperse CNTs, may remain as a residue and thereby degrade the electrical or mechanical properties of the final CNT-derived product. The cohesive assembly, when prepared by the present method, need not contain surfactants. Therefore, the method of the current invention represents a substantial improvement over existing techniques for dispersing CNTs in an aqueous medium.

Furthermore, the carbon starting material is dispersed in the solution that is substantially free of a binding material (e.g. polymers, inorganic or hybrid materials). For industrial use, such binding materials are typically required in order to form a carbon monolith. For example, to form a monolith of activated carbon for use in an electrochemical double layer capacitor (EDLC), a polymer binding material such as PTFE (polytetrafluoroethylene) is needed to hold the carbon particles together. Similarly, to form carbon aerogel monoliths typically requires impregnation with an organic-based aerogel that acts as a binder and is then later removed by pyrolysis. In the method of the current invention, no such material is needed in order to form the cohesive carbon assembly as a monolith. "Substantially free of a binding material," as used herein, means less than 10%, preferably less than 1%, and more preferably less than 0.1% (w/w) of binding material is present relative to the weight of carbon starting material used to prepare the assembly.

In certain embodiments, the carbon-solution dispersion may be applied to a surface after step (b). In one embodiment, the surface comprises a hydrophobic surface (e.g. a surface comprising a dimethyl organosilane, a fluorinated dimethyl organosilane, a fluorinated polymer, Teflon, or a combination thereof). In another embodiment, the surface comprises a hydrophilic surface (e.g. metal (e.g. aluminum, copper, gold, silver, platinum, tantalum, titanium, stainless steel, and other electrode material) surface, glass surface, silicon surface, plastic, and ceramic.) To achieve a self-delaminating CNT wafer, the method further comprises applying the carbon-solution dispersion to a hydrophobic surface having water contact angle of at least about 80°. To achieve a coherent adhesive CNT coating, the method further comprises applying the carbon-solution dispersion to a hydrophilic surface having water contact angle of less than about 80°.

The dispersion may be applied to the surface by any known method, e.g. without limitation, spin-coating, dip-coating, flow-coating, spray coating, casting, or any combination thereof. The spin-coating may be carried out at a spinning speed of about 10 rpm to about 10,000 rpm, or about 300 rpm to about 5,000 rpm for a time of at least about 5 seconds. The dip-coating may be carried out at a withdrawing speed of about 0.01 to about 1.0 cm/s, about 0.1 to about 0.4 cm/s, or about 0.2 cm/s.

In other embodiments, a carbon-solution dispersion may be transferred from one container to another container after step (b). One objective of such transferring is to produce a cohesive carbon assembly of certain desired size and shape. The amount of dispersion transferred, and the size and shape of the container, can be selected to produce assemblies of various sizes, shapes, and thicknesses. Another objective of transferring the dispersion is to produce a large number of individual assemblies of desired size(s) and shape(s) from a single large batch of carbon-water dispersion, thereby increasing efficiency and improving cost performance of the process. The container into which the dispersion is transferred may have surfaces comprising a hydrophobic surface, examples of which are given above. Or, the container into which the dispersion is transferred may have surfaces comprising a hydrophilic surface, as also described above.

The cohesive carbon assembly will form and remain intact (crack- and defect-free) when the ratio of the amount of CNT in the dispersion to the surface area onto which it is applied, is within a certain range. The suitable ratio of amount of CNT to the applied surface area (milligrams per $cm^2$) is between about 0.01 mg and about 500 mg per $cm^2$, and preferably between about 0.1 mg and about 50 mg per $cm^2$. In one embodiment, the CNT-solution dispersion is applied onto a surface inside a container such that the ratio of CNT to bottom surface area of the container is between about 1 and about 5 mg per $cm^2$.

In step (c), the liquid portion of the dispersion is substantially removed, i.e. greater than 99% of the liquid is removed, in a controlled manner, whereby the cohesive assembly of carbon is formed. In order for the cohesive assembly to form, liquid must be removed in a controlled manner. "Removing in a controlled manner," as used herein, refers to removing liquid under conditions such that the dispersed carbon self-assembles into the cohesive assembly of carbon, and the assembly remains intact as a single cohesive monolith throughout the removal process, and after liquid removal is completed. Any method to remove liquid in a controlled manner that allows the self-assembly of the carbon into a cohesive assembly, and allows the assembly to remain as a cohesive monolith after liquid removal is completed, is within the scope of the invention. For example, without limitation, a controlled manner of removing liquid may include evaporation, draining of liquid from the container, or a combination thereof. It is important not to remove liquid so rapidly such that it will disturb or prevent the carbon from forming a cohesive monolith. It is also important not to agitate the mixture during the removal process.

An example of a non-controlled manner of removing liquid is pouring off the water by tipping the container (decanting), as this would clearly disturb the formation of the cohesive assembly and not result in a monolithic form. Another example of a non-controlled manner is boiling of liquid, as the accompanying vapor bubble generation and resultant agitation of the mixture would clearly disturb the cohesive assembly and prevent the monolith from forming. A third example of a non-controlled manner would be direct physical removal of the liquid at or through its exposed top surface in the container, for example, by suctioning through a tube or pipe. The breaking of the surface of the liquid by the tube or pipe would clearly interfere with the self-assembly of the carbon into a monolith.

In one embodiment, the controlled removal of liquid is conducted by evaporation. During the initial stages of this evaporation, the dispersed carbon first nucleates on the top surface of the liquid, and then begins to assemble or coalesce into "islands" of carbon on the surface of the liquid. As evaporation progresses, the islands grow and join together to form larger islands, eventually joining into a single monolithic disc, wafer, or film, i.e., a cohesive assembly of carbon.

If liquid is evaporated too quickly, a cohesive assembly of carbon might not form. In such instances, the carbon may not nucleate on the top surface of the liquid, but may instead remain as a powder or particle residue in the container. Or, the carbon may nucleate on the surface, and islands may begin to form, but they will not coalesce into a monolithic cohesive assembly, and remain as randomly-shaped agglomerates of carbon rather than a cohesive assembly. Or, the islands may coalesce into a monolith, but then later break apart into smaller pieces.

The specific conditions for controlled removal of liquid, that will result in the formation of a cohesive assembly of carbon, depend on the type of the carbon starting material and the ratio of the carbon to the solution, and can be determined experimentally. For example, liquid is removed by evaporation at a suitable pressure, at a suitable temperature, and for a suitable time.

The suitable pressure may be between about 0.001 Torr and about 5,000 Torr, between about 0.01 Torr and about 1500 Torr, between about 1 Torr and about 1000 Torr, between about 100 Torr and about 800 Torr, or at atmospheric pressure (about 760 Torr).

The suitable temperature for controlled removal of liquid may be between about 0° C. and about 100° C., between about 10° C. and about 60° C., between about 20° C. and about 40° C., or at ambient room temperature (between about 15° C. and about 30° C.). In one embodiment, the controlled removal of liquid is achieved at an ambient room temperature between 18° C. and 25° C.

The suitable time for controlled removal of liquid may be between about 1 minute and about 300 hours, between about 10 minutes and about 200 hours, between about 30 minutes and about 100 hours, or between about 1 hour and about 50 hours.

In one embodiment liquid is removed by evaporation at atmospheric pressure. In another embodiment, liquid is removed in a closed system at a pressure below atmospheric pressure. Either condition may be accompanied by heating to accelerate the evaporation of liquid, provided that the rate of evaporation is controlled such that formation of the cohesive assembly of carbon is not disturbed or prevented.

In one preferred embodiment, liquid is removed by evaporation at atmospheric pressure and ambient room temperature (ambient conditions), by simply exposing the carbon-solution dispersion to the ambient environment. This may be achieved whether the dispersion is applied to a surface or enclosed in a container. In this embodiment, the evaporation is controlled only by the ambient conditions.

The evaporation of liquid may alternatively be controlled to form a cohesive assembly, by controlling the ambient relative humidity around the carbon-solution dispersion. This may be achieved by, for example, enclosing the dispersion in a controlled humidity chamber. This approach is especially suitable when the dispersion is applied to a surface as a coating or film. Humidity control may also be achieved by, for example, placing a partial barrier enclosing the container in which the dispersion is held.

The evaporation of liquid may alternatively be controlled to form a cohesive assembly, by monitoring the evaporation rate of liquid and maintaining it within a range that will not prevent or disturb the formation of the assembly. The lower end of the operable range of evaporation rates is not particularly limited, except that a very low rate will result in an impractically long time to produce the cohesive assembly. The evaporation of liquid typically follows the classic and well-known theory of two-stage drying of porous bodies first proposed by Thomas .K. Sherwood in "The Drying of Solids—I", *Industrial Engineering and Chemistry* 21, 1 (1929), 12-16, and in "The Drying of Solids—II", *Industrial Engineering and Chemistry* 21, 10 (1929), 976-980. During the first drying stage, also known as the Constant Rate Period, the evaporation rate is preferably between about 0.01 and about 50 milliliters/minute (ml/min), more preferably between about 0.10 and about 5.0 ml/min. During the second drying stage, also known as the Falling Rate Period, the evaporation rate is preferably between about $5 \times 10^{-5}$ ml/min and about $5 \times 10^{-2}$ ml/min, more preferably between about $5 \times 10^{-4}$ and about $7 \times 10^{-3}$ ml/min.

Typically, greater than 99% of liquid is removed by evaporation. Any remaining liquid may optionally be removed after evaporation, by rinsing the cohesive assembly with water or an organic solvent such as ethanol or isopropanol, and then drying the assembly either at room temperature or with mild heating in an oven.

A cohesive carbon assembly formed inside a container may be removed from the container manually or by lightly rinsing the inner surfaces of the vessel with a fluid such as a dilute acid, base, aqueous solution, or organic solvent. The product assembly may then receive a final drying at atmospheric pressure or under vacuum, which may be accompanied by mild heating. Typically, cohesive assemblies formed on a hydrophobic surface will be easily removed from the surface or container, and will require little or no rinsing. Cohesive assemblies formed on hydrophilic surface will typically require at least some rinsing or mechanical force to remove them from the surface or container.

Characterization of Cohesive Carbon Assemblies

Cohesive carbon assemblies prepared by the method of the invention are characterized by the substantial absence of surfactants during the preparation and in the final product.

Cohesive carbon assemblies prepared by the method of the invention are also characterized by the absence of halogen residue. Assemblies prepared by previously disclosed methods employing halogens as the dispersing solvent typically retain a large amount of halogen as a residue in the assembly. Such residue may be present as solid free halogen deposited on the assembly, or as halogen molecules bonded to the carbon structure. In either form, the halogen residue can degrade the performance and usefulness of the assembly, by interfering with its electronic properties. In particular, such residue may cause increased contact resistance when the assembly is placed in contact with another component, such as a current collector in a capacitor, fuel cell, or battery. Furthermore, the amount of residue that may be present on the assembly is highly unpredictable, so the use of halogens may result in inconsistent properties and performance among different assemblies. It is thus highly advantageous to have a cohesive carbon assembly prepared using a dispersing medium that does not leave such residue. Use of an aqueous solution, and pure water in particular as the dispersing medium, reduces or eliminates this residue.

Cohesive carbon assemblies comprising CNTs, prepared by the method of the invention, feature high effective carbon packing density compared to other known CNT assemblies. The cohesive carbon assemblies typically have effective CNT packing density of at least about 0.5 g/cm$^3$, often have densities higher than 1.0 g/cm$^3$, and have shown densities as high as 1.5 g/cm$^3$. For example, the cohesive carbon assemblies have effective CNT packing density of between about 0.3-1.9 g/cm$^3$, preferably between about 0.5-1.5 g/cm$^3$, and more preferably between about 0.8-1.5 g/cm$^3$ or between 1.0-1.5 g/cm$^3$. This high density imparts these assemblies with good mechanical strength and integrity. This high density also contributes to their superior electrical properties; in particular their low resistivity compared to other known CNT assemblies.

To determine the effective CNT packing density in a CNT-derived carbon assembly, first the apparent density of the assemblies is determined by carefully measuring the weight of the assembly using a standard analytical balance, then measuring the dimensions of the assembly using a digital micrometer or optical or scanning electron microscope, then calculating the volume of the sample from the dimensions, and dividing the weight by the volume. This calculation provides the apparent density of the assembly. Alternatively, the apparent density may be determined using a density balance and Archimedes' principle. Then, using one of various methods such as energy dispersive x-ray spectroscopy (EDS), neutron activation analysis (NAA), or thermogravimetric analysis (TGA), the weight fraction of carbon (i.e., CNTs) in the assembly can be determined. Finally, the effective packing density of CNTs is calculated by multiplying the apparent density by the weight fraction of carbon in the assembly.

The assemblies can be produced in a desired size or shape, which is determined by the amount of carbon used to prepare the assembly, and by the size and shape of the container in which the carbon assembly is prepared. This may allow the assemblies to be used in various applications requiring carbon assemblies of various shapes and sizes. When liquid is removed from the dispersion, the carbon typically self-assembles in the shape and size of the bottom of the vessel in the horizontal plane, with a vertical, i.e., perpendicular thickness that is determined by the amount of carbon used and the size of the container. Greater amounts of carbon will produce a thicker wafer or disc-like cohesive assembly, while less carbon will produce a thinner, film-like assembly. Decreasing or increasing the diameter or cross-sectional area of the container used to prepare the assembly has similar effects on assembly thickness. In certain embodiments, the assembly has a thickness of about 0.02 µm to about 2,000 µm, or about 0.1 µm to about 500 µm. In one embodiment, the assembly is a self-delaminating assembly having a thickness of about 0.1 µm to about 2000 µm, about 1 µm to about 500 µm, or about 10 µm to about 50 µm. In another embodiment, the assembly is an adhesive assembly having a thickness of about 0.02 µm to about 2000 µm, about 0.02 µm to about 500 µm, or about 0.02 µm to about 50 µm.

Cohesive carbon assemblies may be prepared by the method of the present invention with sufficiently small thickness, such that they show significant optical transmittance. Above a certain thickness, optical transmittance is negligible, and as thickness is decreased, the transmittance increases, to a maximum of greater than 90% in the wavelength range of 500-2000 nm. The transmittance of a particular cohesive assembly depends on factors such as the type of carbon(s) present in the assembly, the packing density of the assembly, and processing parameters such as drying conditions, substrate type, etc. Generally speaking, a cohesive carbon assembly prepared by the present method having thickness between about 0.02 µm and about 1.0 µm may have optical transmittance of up to about 97%. In one embodiment, a cohesive carbon assembly is prepared by the method of the invention, having thickness between about 0.10 and 0.15 µm, and optical transmittance of between about 80 and 90% between 500 and 2000 nm.

The cohesive carbon assemblies prepared by the method of the invention also feature low electrical resistivity compared to other carbon assemblies. These assemblies typically have resistivity of less than about 0.1 Ω-cm, about 0.02-0.05 Ω-cm, and an electrical sheet resistance of less than about 2,000Ω per square, or between about 8 and about 17Ω per square. This low electrical resistivity along with mechanical strength and integrity may allow various applications of these assemblies, for example, as electrodes for batteries or supercapacitors, or as electromagnetic interference (EMI) shielding materials. This low resistivity is related to the high effective carbon packing density of the assemblies in that as this density increases, empty space between individual carbon entities such as nanotubes, tube bundles, or graphite platelets decreases, and the area of contact between these carbon entities increases. This naturally leads to more efficient and higher current flow through the assembly, thereby decreasing its resistivity.

Resistivity of the cohesive assembly is determined as follows: From each assembly, a sample of rectangular or square geometry is cut that possesses lengths greater than 1 cm on all sides. The sample is mounted in a sample mount, and two electrical contact pairs (two current carrying and two voltage sensing) are directly compressed to the sample, in a standard Kelvin-type (4-point) probe configuration. The sample is positioned such that the four metal tips of the four-point probe make direct contact with the sample without puncturing through it.

A constant current is made to flow the length of the sample by using a high impedance current source. The current source is typically set to apply a current of $0.1 \times 10^{-3}$ A, $1 \times 10^{-3}$ A, $10 \times 10^{-3}$ A, or $100 \times 10^{-3}$ A. The voltage drop across the sample is measured using a high impedance digital voltmeter. The surface (sheet) resistance, $R_s$ in Ω (or Ω/sq), of the sample is the ratio of the stable voltage registering on the voltmeter, V, to the value of the output current of the current source, I, multiplied by the geometric factor $\pi/\ln 2 \approx 4.53$:

$$R_s = 4.53(V/I).$$

By measuring the thickness (t) of the sample, using a profilometer, digital micrometer, or scanning electron microscope, the electrical resistivity ρ of the sample in Ω-cm, can be calculated using the formula:

$$\rho = R_s(t)$$

Additionally, cohesive carbon assemblies prepared by the method of the invention using carbon starting material comprising CNTs (e.g. SWCNTs) display no more defects than the carbon starting material. A known technique useful for evaluating the quality of CNTs, i.e., the concentration of structural defects and amorphous carbon impurities included therein, is by measuring the intensity ratio of two characteristic Raman infrared spectral peaks, called the G/D ratio. The G-line is a characteristic feature of the graphitic layers and corresponds to the tangential vibration of the carbon atoms. The D-line is a typical sign for defective graphitic structures. When determining the quality level of a CNT sample via Raman spectroscopy, the absolute intensities of the G and D band peaks are not particularly relevant. Rather, the ratio of the intensity of the two peaks is the relevant measure. The comparison of the ratios of these two peaks' intensities gives a measure of the quality of the CNT samples. Generally, the G/D ratio is the ratio of good to bad CNT peaks. Thus, CNTs having a higher G/D indicate a lower amount of defects and a higher level of quality.

A G/D ratio is typically determined using a Raman spectroscopy technique. Any of various commercially available instruments may be used to measure the G and D band intensities and to calculate the G/D ratio. One example of such an equipment is available from HORIBA Jobin Yvon Inc., Edison, N.J., under the model name LabRAM ARAMIS.

In a CNT sample, the G/D ratio may change after treatment. The present method has the advantage that the G/D ratio of the formed cohesive carbon assembly is about the same or greater than the G/D ratio of the carbon starting material, indicating that the method does not introduce structural defects during the process.

Applications of Cohesive Carbon Assemblies

Another aspect of the invention relates to an article comprising a substrate and a cohesive carbon assembly coated onto at least one surface of the substrate, wherein the cohesive carbon assembly has been prepared by the method described supra.

The cohesive carbon assembly may be otherwise treated after its fabrication, in order to enhance its performance for certain applications. For example, for application as a fuel cell electrode, a coating of metal particles, such as platinum, may be advantageous for its catalytic properties. For battery electrode applications, metal particle coatings such as iron, platinum, palladium, nickel, lithium, or other appropriate metals may be desired. Such particle coatings may be accomplished using a method disclosed by Grigorian et al in US Patent Application Publication US 2009/0015984A1, which is hereby incorporated by reference.

The cohesive carbon assembly of the present invention has particular advantages over other types of carbon assemblies for use as an electrode or current collector in electrochemical capacitors, fuel cells, or batteries. These advantages include its inherent mechanical strength and integrity, low electrical resistivity, ability to be fabricated and/or further modified to a desired shape and size, and high carbon packing density that results in excellent energy storage capabilities (i.e., power density and energy density).

The cohesive carbon assembly is appropriate for use as an electrode in a capacitor or a capacitor cell, which are used interchangeably in this application, due to its desirable combination of electrical and mechanical properties. The capacitor may be of any type that comprises two electrodes separated by an insulating material. The capacitor may be a simple electrostatic capacitor with a bulk dielectric material separating the two conducting electrodes, or an electrolytic capacitor, in which one or both of the electrodes comprise(s) an electrolyte. The cohesive carbon assembly is especially suitable for use as an electrode in an electrochemical double-layer capacitor (EDLC), sometimes referred to as a "super-capacitor" or "ultracapacitor".

The cohesive carbon assembly, and in particular the assembly comprising carbon nanotubes, may be altered after fabrication by the invented method into an electrode of suitable size or shape for direct installation into a capacitor cell. The electrode may be disc-shaped, i.e. round or ovoid, or it may be a polygon having three or more sides. The size and shape are determined only by the size and shape of the capacitor device in which it will be used. The thickness of the electrode is not particularly limited, but certain thicknesses may be preferable for use in capacitor devices. If the electrode is too thick, resistance of the electrode may be too high or energy transfer will be inefficient. If it is too thin, it will not have the necessary mechanical integrity or energy storage potential for capacitor use. Generally, the thickness is preferably between about 0.02 µm and about 2,000 µm, or between about 0.1 µm and about 500 µm. In one embodiment, the assembly is a self-delaminating assembly having a thickness of about 0.1 µm to about 2000 µm, about 1 µm to about 500 µm, or about 10 µm to about 50 µm. In another embodiment, the assembly is an adhesive assembly having a thickness of about 0.02 µm to about 2000 µm, about 0.02 µm to about 500 µm, or about 0.02 µm to about 50 µm.

The cohesive carbon assembly may be optionally purified of metallic impurities prior to use as a capacitor electrode. Specifically, for an assembly comprising carbon nanotubes, removal of metallic impurities that are residues of the CNT synthesis process may improve the electrical and energy storage properties of the assembly. This purification may be accomplished by various means, with treatment with a halogen gas, and chlorine gas in particular, being the preferable method. The parameters of this treatment process are not particularly limited, provided the carbon is not damaged or degraded during the process.

To evaluate the performance of a cohesive carbon assembly as a capacitor electrode, one electrode may comprise a cohesive carbon assembly in an asymmetrical capacitor cell, or two electrodes may each comprise a cohesive carbon assembly in a symmetric capacitor cell. The method of evaluating the performance of the cohesive carbon assembly as a capacitor electrode is not particularly limited, and there are various standard methods known in the field. Typically, the capacitor cell comprising the two electrodes separated by an insulating material is assembled with metal plates as current collectors attached to the outer surfaces of the electrodes. The cell is then submerged in an appropriate electrolyte and a voltage is applied. For EDLCs, the preferable applied voltage (absolute value) is between 0 and 2 volts, or between 0 and 4 volts, to evaluate performance for consumer electronics and vehicle applications. Analytical methods used to evaluate the electrode performance may include leakage current measurement, electrochemical impedance spectroscopy (also known as dielectric spectroscopy), charge/discharge cycling using commercially available test equipment, and the like.

To determine the performance advantage of the cohesive carbon assembly as a capacitor electrode, the properties measured are compared to those of capacitors comprising electrodes of other standard materials such as activated carbon, or other types of CNT-based electrodes such as CNT forest-derived materials. Cohesive assemblies of carbon prepared by the present method in general show superior power performance as capacitor electrodes, compared to activated carbon electrodes and other types of CNT-based electrodes. The superior performance includes lower leakage current and faster discharge time, and a better combination of power density and energy density, important parameters for electric vehicle and consumer electronics applications. Furthermore, the cohesive assemblies possess the necessary mechanical integrity to be packaged directly into sealed capacitor cells, whereas the other CNT-based electrodes do not.

Similarly as for a capacitor, the cohesive carbon assembly of the present invention is suitable for use as an electrode in a battery. The battery may be of any type comprising two electrodes separated by electrolyte. Of particular interest is the Li-ion battery type, in which the cohesive carbon assembly is suitable for use as the anode or cathode material, or both. As for the capacitor application, the size, shape, and thickness of the battery electrode comprising the cohesive carbon assembly are not particularly limited. Preferred thicknesses are also similar to those for capacitor electrodes.

The cohesive carbon assembly may be used as a battery electrode in its as-prepared form, i.e. as an assembly comprising nearly pure carbon. Or, the assembly may be further treated after it is fabricated by, for example, coating with metal particles using the method described in US Patent Application Publication US 2009/0015984A1. The metal coating may be selected such that the assembly is suitable for use as the anode, or it may be selected such that the assembly is suitable for use as the cathode. The appropriate metal coating depends on the overall design of the cell.

In its as-prepared form, a cohesive carbon assembly of carbon nanotubes, and more preferably, a cohesive assembly of SWCNT, is especially appropriate for use as the anode in a Li-ion battery cell, with a corresponding cathode comprising one or more Li-containing oxides such as $LiCoO_2$, $LiFePO_4$, or $LiNiCoAlO_2$. The electrode comprising the cohesive carbon assembly requires no binder material and can be installed in a battery cell in its as-prepared form.

A battery containing a cohesive carbon assembly electrode may be performance tested using a standard method such as is described by Y. NuLi et al in "Synthesis and characterization of Sb/CNT and Bi/CNT composites as anode materials for lithium-ion batteries," *Materials Letters* 62 (2008) 2092-2095, or by J. Yan et al in "Preparation and electrochemical properties of composites of carbon nanotubes loaded with Ag and $TiO_2$ nanoparticle for use as anode material in lithium-ion batteries," *Electrochimica Acta* 53 (2008) 6351-6355. In this manner, the performance of a cohesive carbon assembly-based lithium-ion battery anode is thereby compared to the performance of lithium-ion battery anodes composed of other materials such as graphite, hard carbon (i.e. diamond-like carbon), titanate, silicon, germanium, other CNT-based electrodes that require binder or structural support, and the like.

The cohesive carbon assembly of the present invention is also suitable for use as an electrode in a fuel cell. In a PEM-type fuel cell, the electrode comprises a catalyst support layer and a gas diffusion layer (GDL). The cohesive carbon assembly, as described earlier, has low resistivity and high mechanical strength and integrity. Furthermore, it exhibits sufficiently high pore volume to allow the needed diffusion of gaseous species (hydrogen, oxygen, water vapor) for fuel cell use. The total pore volume of the assembly comprising SWCNT is typically greater than 1.0 $cm^3/g$, often greater than 1.5 $cm^3/g$, and has been observed to exceed 2.0 $cm^3/g$. Total pore volume correlates with total porosity, and approximately correlates with gas permeability. Therefore, the cohesive carbon assembly, and in particular the SWCNT assembly, is appropriate for use as either the catalyst support or the GDL, or as both simultaneously.

The size and thickness of the cohesive carbon assembly, for use in a fuel cell, are not particularly limited. However, the thickness should be selected such that the desired level of gas permeability is maintained, and, when used as the catalyst layer, such that the desired level of catalytic activity through the layer is achieved. The thickness of the cohesive carbon assembly of this invention when used as a catalyst layer in a fuel cell is typically 5-20 µm thick. The thickness of the cohesive carbon assembly of this invention when used as a GDL in a fuel cell is typically 100-300 µm thick.

For use as a catalyst support in a fuel cell, the cohesive carbon assembly is typically coated with metal particles that act as the catalysts for the electrochemical reaction. The type of metal particles is chosen based on whether the electrode is to be the cathode or anode in the fuel cell. For example, if the assembly is to be the anode, the metal may be platinum. If the assembly is to be the cathode, the metal may be nickel. The coating may be accomplished by any appropriate method, for example, by the method described in US Patent Application Publication US 2009/0015984A1. This coating method comprises two essential steps: (1) the assembly is treated with a halogenated precursor, such as platinum iodide ($PtI_2$), nickel iodide ($NiI_2$), palladium iodide ($PdI_2$), or the like, to form a halogenated intermediate; (2) residual halogen is removed and the metallic species deposited on the assembly are reduced to pure metal by heating combined with hydrogen gas treatment.

To evaluate the performance of the cohesive carbon assembly as a catalyst support, GDL, or both, a PEM-type fuel cell is assembled with the cohesive carbon assembly component in place of the standard material typically used for that component. For example, if the cohesive carbon assembly is the catalyst support, then it is coated with the catalyst metal particles and then installed in the fuel cell in place of the standard catalyst support, usually Pt-coated or Ni-coated carbon black. If the cohesive carbon assembly is the GDL, then it is installed in the fuel cell in place of the standard GDL, usually carbon paper or carbon cloth. If the cohesive carbon assembly is both the catalyst support and the GDL, it is installed in place of both standard components. The fuel cell with the cohesive carbon assembly installed may be performance tested by any standard method, such as that described by B. Fang et al in "Nanostructured PtVFe catalysts: Electrocatalytic performance in proton exchange membrane fuel cells," *Electrochemistry Communications* 11 (2009) 1139-1141. Performance parameters such as cell voltage and power density vs. current density are thus compared with those of standard fuel cells or fuel cells containing other potential alternative catalyst support/GDL materials.

Energy storage devices such as capacitors, batteries, and fuel cells, typically comprise a current collector and an electrode on one side of an insulating material or an electrolyte, and another current collector and another electrode on the other side of the insulating material or electrolyte. For example, in an electrostatic capacitor, the separating material is an insulating material, whereas in EDLCs, batteries, and fuel cells, the separating material is an electrolyte. The electrolyte in and EDLC, battery, or fuel cell is divided by a thin membrane allowing ionic conduction between the electrodes. The cohesive carbon assembly of the present invention is appropriate for use as a current collector in these energy storage devices, due to its low resistivity, good mechanical properties, and ability to be fabricated into a desired shape and size.

The cohesive carbon assembly may further be used concurrently as a free-standing electrode and a current collector. A free-standing electrode, as used herein, refers to an electrode containing the cohesive carbon assembly as the only conductive material. The advantage of this is that the entire mass contributes to the usable electrode capacity. This is in contrast to a conventional electrode where the usable electrode capacity is decreased because of mass averaging of the active material composite layer and a metal current collector. Typically, the current collector is an aluminum or copper plate, with notably higher mass density (2.7 and 8.8 $g/cm^3$, respectively, for Al and Cu) than that of the CNT electrode (~0.7 $g/cm^3$), which in turn adds significant weight to the device.

Another advantage for free-standing electrodes is the ability to adjust the electrode thickness that might lead to performance improvement. For example, in electrochemical double-layer capacitors (EDLC), thinner electrodes having lower resistance provide higher power density. This approach to performance improvement is not feasible with conventional designs due to the relative increase in the mass percent of the current collector.

Other advantages, more specific to the design of particular energy storage devices, are foreseeable. For example, in a battery, elimination of the copper substrate would allow for cycling below 2.5 V (the typical potential where oxidation of the copper substrate initiates), thus increasing the depth of discharge and creating the opportunity to maintain a near-zero volt state-of-charge for prolonged storage. In general, substitution of metal current collectors with the cohesive carbon assembly of the present invention enables entirely new designs for these devices.

The invention is illustrated further by the following examples that are not to be construed as limiting the invention in scope to the specific procedures or products described therein.

EXAMPLES

Example 1

Fabrication of Free Standing CNT Wafer from Aqueous Dispersion Using Sonication and Microfluidization Preparation of Aqueous CNT Dispersion As-received amide-functionalized SWCNT (P9 SWNT, CSI Inc., Riverside, Calif.) was ground by mortar and pestle. Three masses of the ground material, 240 mg, 200 mg, and 160 mg, were separately combined with 40 g each of de-ionized (DI) water in a beaker, to create CNT/water dispersions with ratios (mg/g) of 6:1, 5:1, and 4:1 respectively. To facilitate dispersion of the CNT loadings in water, each mixture was sonicated for 2 cycles of 10 minute duration (total 20 minutes) using a probe sonicator (V600, Sonics & Materials, Inc., Newtown, Conn.). The probe tip was directly immersed into the CNT/water mixture for sonication. The suspension became black after 10 seconds of sonication.

Immediately after sonicating, the resulting CNT/water dispersions were passed once through a microfluidizer (M-110Y, Microfluidics Corporation, Newton, Mass.), and collected as the effluent stream by flushing with DI water. A stock dispersion volume of about 40 mL was collected from each loading after one pass and used as the primary CNT/water dispersion for casting. No precipitation, sedimentation, or phase separation was observed in the microfluidized dispersions, which resembled commercial conductive inks. Additional volumes of aqueous CNT dispersion, referred to as residue dispersions, were collected from the microfluidizer during flushing with DI water to remove all trace of CNT from the instrument.

Typically, introducing 40 mL of stock CNT dispersion into the microfluidizer (which is close to its minimum chamber fill volume) requires about four flushes with water to completely remove residual CNT from the instrument. These flushing steps produce an output of about 160 mL of CNT dispersion volumes of varying dilution. Each of these diluted CNT dispersions can be used for successive wafer fabrication. The first 40 mL collected volumes from each prepared CNT/water ratio dispersion were designated primary CNT dispersions, while the subsequent diluted dispersions collected by flushing were designated residual dispersions R1, R2, R3 etc.

Preparation of CNT Assemblies

Figure 2:
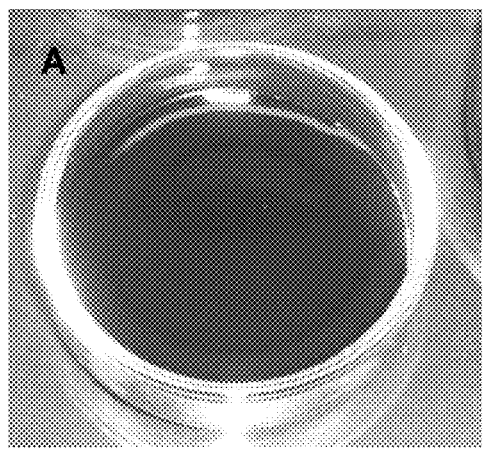
FIG. 2 shows two optical images (A) and (B), of an aqueous CNT dispersion at different stages of water evaporation and formation of a cohesive CNT assembly, as described in Ex. 1.
Figure 2:
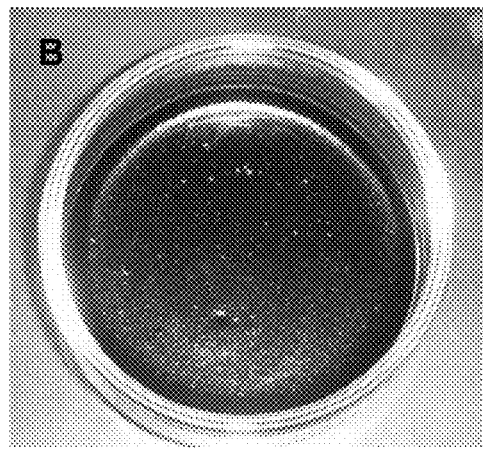

The primary microfluidized CNT/water dispersions from each loading were partitioned into the following volumes for casting: 5 mL, 10 mL, and 15 mL. Each volume was cast into a previously cleaned Pyrex dish of 5 cm diameter and placed into a containing dish (without cover) within a fume hood. Initially, water was evaporated from the nine aqueous CNT dispersions under ambient conditions (23° C.) without any covering, as shown in FIG. 1. Unrestricted evaporation was continued until there was a visible change in optical density and viscosity. FIG. 2 captures these changes as the water evaporated, comparing a dispersion from which less water has evaporated (A), to one from which more water has evaporated (B). When these changes to dispersions were observed, the dish and dispersion were covered with aluminum foil that was perforated with an array of small holes using a 20G needle, to reduce the evaporation rate of the water.

Figure 3:
FIG. 3 shows two optical images (A) and (B), of nine aqueous CNT dispersions at different stages of water evaporation and formation of cohesive CNT assemblies, as described in Ex. 1.
Figure 3:
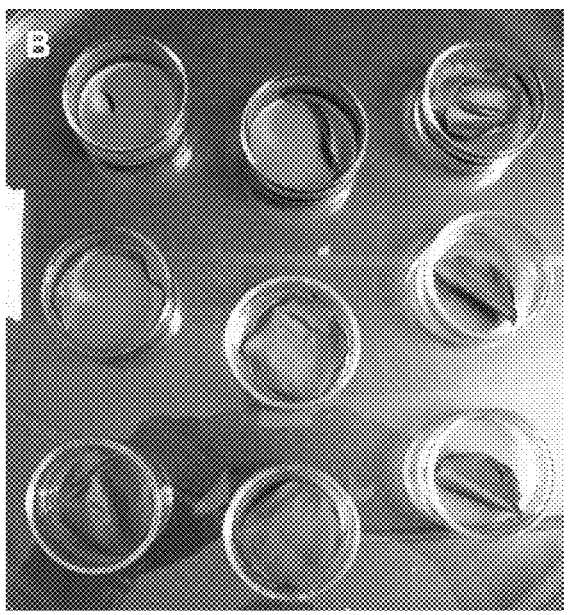
Figure 4:
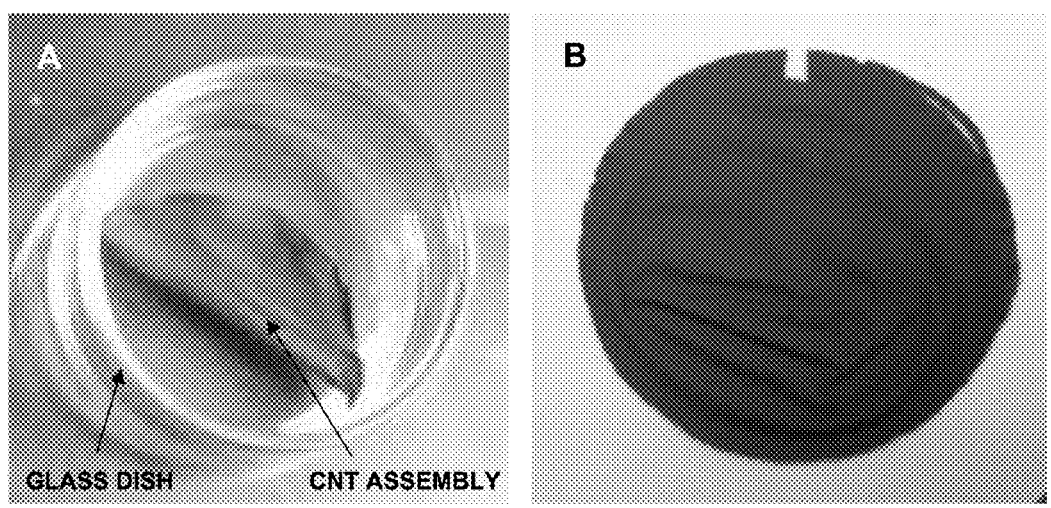
FIG. 4 shows optical images of (A) an intact but curled cohesive CNT assembly, and (B) the same assembly after being soaked with ethanol, pressed flat, and dried, as described in Ex. 1.

Water evaporated from the CNT/water dispersions in order of their volume capacities, that is, the 5 mL dispersions dried first, followed by the 10 mL dispersions, and finally the 15 mL dispersions. After 7 days, water was completely evaporated from all but the three largest volumes of dispersion (FIG. 3(A)), and the CNT had formed into intact cohesive carbon assemblies (wafers). At this stage, the foil coverings were removed from the three remaining wet dispersions and water was allowed to evaporate unrestricted in open air. After a further 5 days, these three dispersions also formed intact CNT wafers, with some curling (FIG. 3(B)). All wafers formed intact, without cracks or fractures. The curled wafers were restored to flat by wetting them with ethanol, then pressing them between glass plates and allowing to dry at room temperature. After this procedure, the wafers remained flat and did not curl again (FIG. 4).

Wafers produced from 5 mL dispersions had final thicknesses between about 15 and 20 µm, those produced from 10 mL dispersions had final thicknesses between about 25 and 45 µm, and those produced from 15 mL dispersions had final thicknesses between about 45 and 60 µm. Wafer thickness also roughly correlated with the total amount of CNT (and with the CNT:area ratio), especially when the ratio was between about 1 and 3 mg CNT per cm² of container area.

Example 2

Fabrication of Free Standing CNT Wafer from Aqueous Dispersion Using Refluxing and Microfluidization Preparation of Aqueous CNT Dispersion Approximately 400 mg of carboxyl-functionalized SWCNT (P3 SWNT, CSI Inc.) were combined with 80 mL of DI water in a round bottom flask to create a CNT/water dispersion with ratio of 5:1 (mg/g). The CNT/water mixture was refluxed in boiling water while stirring for 4 hours. The resulting dispersion was divided into two 40-mL portions, and each of these was passed through the microfluidizer one time. For each 40 mL portion, the primary and three residual dispersions (R1-R3) were collected as the effluent streams by flushing with DI water as described in Example 1. CNT concentrations in the residual dispersions were determined by casting fixed volumes of each into dishes and then weighing the resulting assemblies after completely evaporating the water. The CNT concentrations of dispersions R1, R2, and R3 were determined to be 2.0, 0.8, and 0.4 mg/g, respectively.

Preparation of CNT Assemblies

Figure 5:
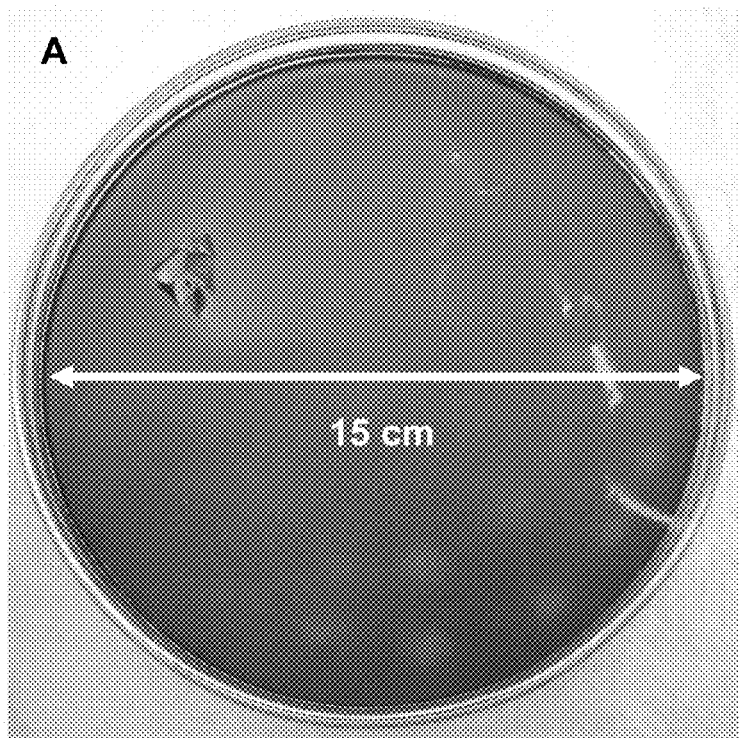
FIG. 5 shows optical images (A), (B), and (C) of cohesive CNT assemblies of various sizes, prepared as described in Ex. 2.
Figure 5:
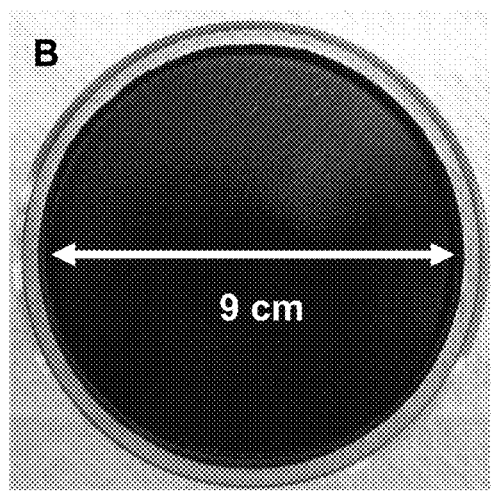
Figure 5:
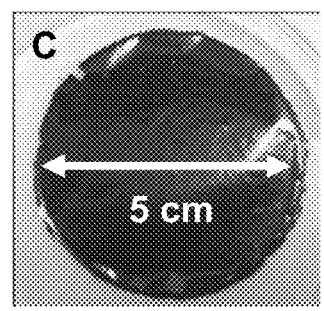

One of the two 40 mL primary CNT/water dispersions was cast into a Pyrex dish of 15 cm diameter, and covered with perforated Al foil. The water was allowed to evaporate under ambient conditions, and a dry, monolithic CNT wafer formed after 9 days. Some discontinuities were present in wafer, but it was completely cohesive and intact otherwise. The thickness was 22 µm. This CNT wafer is shown in FIG. 5(A).

The second 40 mL primary CNT/water dispersion was partitioned into four 5 mL portions and one 15 mL portion. The 15 mL portion was cast into a 9 cm Pyrex dish, and two of the 5 mL portions were cast into two 5 cm Pyrex dishes. The dishes were covered with perforated Al foil and the water was evaporated under ambient conditions. FIGS. 5(B) and 5(C) show resulting dry, intact, cohesive 9-cm and 5-cm CNT wafers that formed u after 6 days. The thickness of the 9-cm wafer was 23 µm. The thickness of the 5-cm wafers was between 20 and 25 µm.

Example 3

Fabrication of Adherent CNT Assemblies on Aluminum Substrates

Aqueous CNT (CSI Inc. P3 SWNT) dispersions were prepared via the sonication-microfluidization route (Example 1) and the refluxing-microfluidization route (Example 2).

For the aqueous CNT dispersion prepared according to Example 1, residual dispersions R1, R2, and R3 were collected after microfluidization, as described in Example 2. About 5 ml of the first (R1) residual dispersion were cast directly into an aluminum foil pan 4 cm in diameter, which had been etched with dilute NaOH solution for 2 minutes to promote adhesion of the CNT assembly. The etched Al pan was lined along its inside periphery with tape to expose only the base for CNT contact and adhesion. To another similarly treated Al pan, 5 mL of R2 CNT/water dispersion were cast. Water was allowed to evaporate from the cast dispersions under ambient conditions of temperature and pressure. Evaporation completed in about three days.

For the aqueous CNT dispersion prepared according to Example 2, about 5 ml each of the primary dispersion were cast into two NaOH-etched aluminum foil pans, and water was evaporated under ambient conditions of temperature and pressure. Evaporation completed in about three days.

Figure 6:
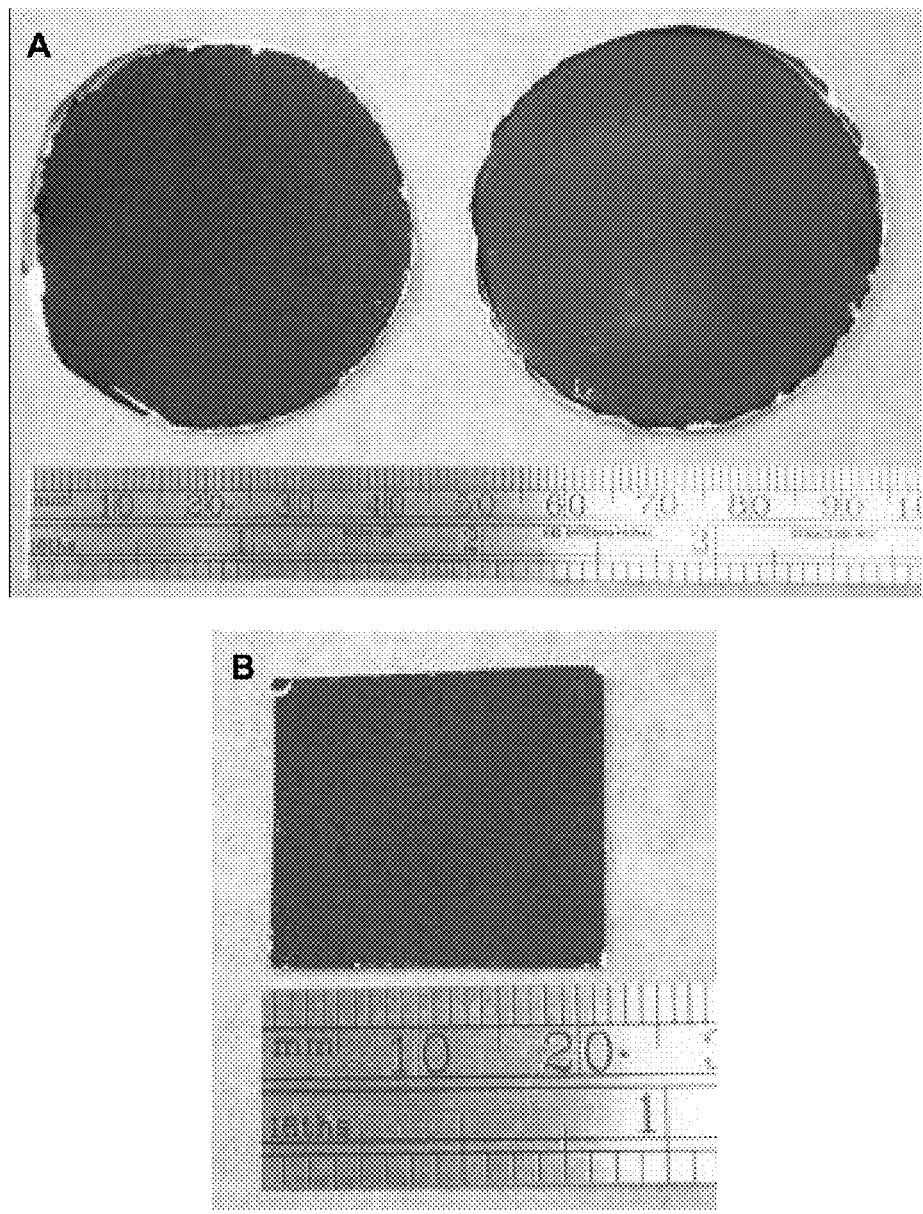
FIG. 6 shows optical images (A) and (B) of cohesive, adherent CNT assemblies deposited directly on aluminum foil substrates, prepared as described in Ex. 3.

After evaporating the water, the cast dispersions all formed into intact CNT assemblies that adhered to the aluminum pans. The CNT assemblies had no cracks, fractures, or other visible discontinuities, as shown in FIG. 6(A). Shapes such as squares were cut from the assemblies for testing, as shown in FIG. 6(B). The CNT assemblies were about 15 µm thick.

Example 4

Fabrication of Adherent CNT Assemblies on Polymer Substrates

Figure 7:
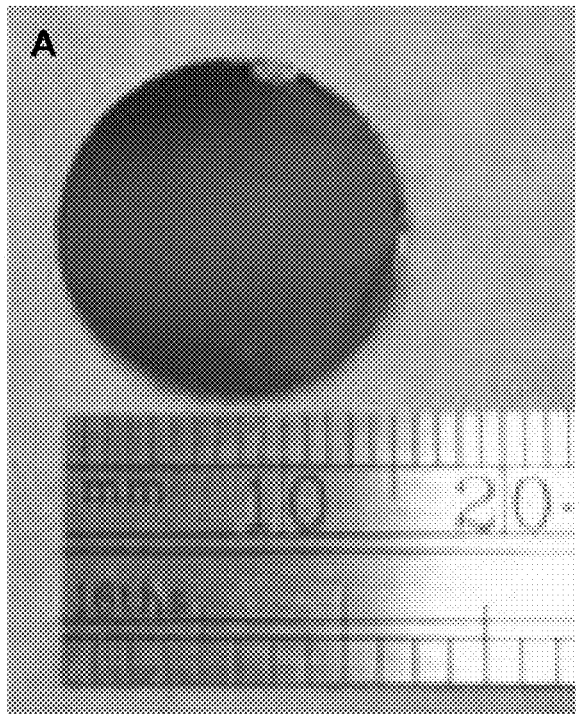
FIG. 7 shows optical images of a cohesive, adherent CNT assembly on polyethylene terephthalate (PET) film, prepared as described in Ex. 4; (A) CNT side, (B) PET side.
Figure 7:
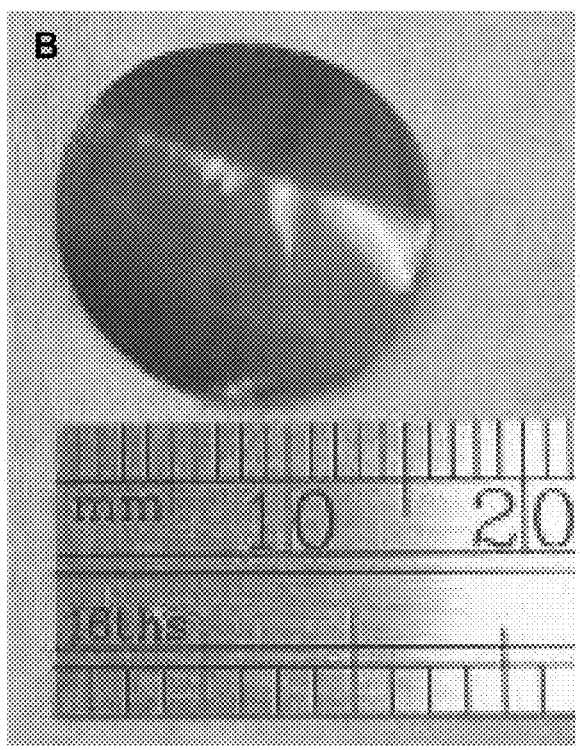

An aqueous CNT dispersion was prepared via the sonication-microfluidization route described in Example 1. The residual dispersions R1, R2, and R3 were collected after microfluidization as described in Example 2. About 5 mL of the R1 dispersion were cast into a 5-cm diameter Pyrex dish into which had been placed a circular insert of polyethylene terephthalate (PET) film. Water was evaporated from the dispersion under ambient conditions and was completely removed after three days. The CNT formed into an intact assembly which partially adhered to the PET film. The adherent portions were flexible and did not crack, fracture, or flake when the film was flexed. A ⅝-inch disk was cut from the adherent portion of the CNT/PET film structure and remained intact and flexible (FIG. 7). The thickness of the CNT assembly was 17 µm.

Example 5

Continuous Fabrication of CNT Assemblies

Figure 8:
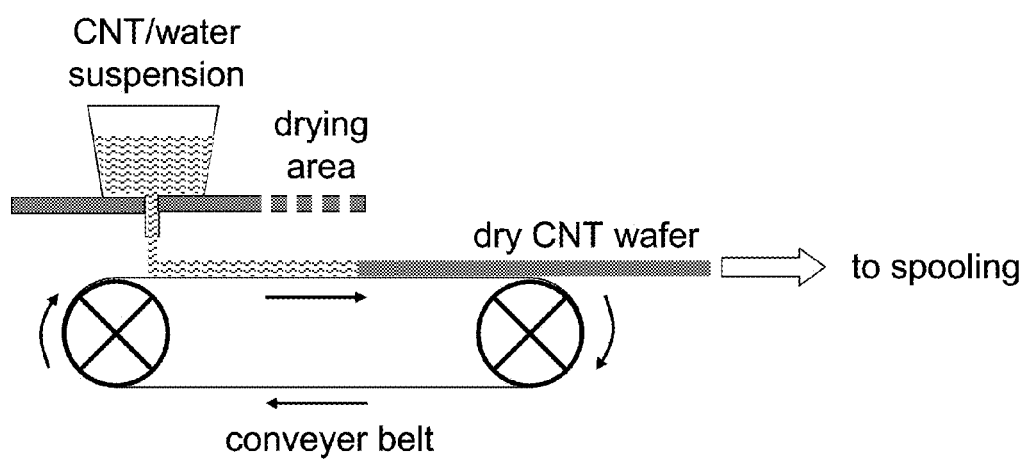
FIG. 8 shows a schematic diagram of an apparatus for continuous CNT wafer fabrication, as described in Ex. 5.

A schematic diagram of an apparatus for continuous CNT wafer fabrication is shown in FIG. 8.

An aqueous CNT dispersion is prepared according to the method described in Example 2. The CNT/water dispersion is continuously added to a tank or hopper. From the tank or hopper, the dispersion is continuously dispensed at a controlled rate onto a conveyor belt that is moving at a controlled speed. The dispersion feed rate and belt speed are controlled to produce a CNT assembly of desired thickness.

To produce a CNT assembly on a substrate (such as polymer film or metal foil), the conveyor belt feeds the desired substrate material with chosen thickness, size, and shape. After the dispersion is fed onto the substrate, the belt moves the dispersion and substrate through an evaporation area at a controlled rate. Water is evaporated at ambient room temperature and pressure with optional heating to increase drying rate. The CNT form into an assembly which is adherent on the substrate, and emerges from the evaporation area as a strip or ribbon. The assembly is then continuously collected by spooling. Optionally, the assembly is directed to a cutter to produce a desired shape and size of individual assemblies.

To produce a continuous, free-standing CNT assembly, the conveyor belt surface material is selected or treated such that it is sufficiently hydrophobic to prevent the CNT assembly from adhering to it. Optionally, the conveyor belt has a groove or depression parallel to the direction of motion, into which the dispersion is dispensed. Water is evaporated from the dispensed dispersion as above and the CNT assembly forms, emerging as a free-standing strip or ribbon, which is collected by a spool. Optionally, the assembly is directed to a cutting apparatus to produce a desired shape and size of individual assemblies.

Example 6

Coherent SWCNT Coating Films on Substrates (Spin-Coated)

One (1) ml of the aqueous CNT dispersion with CNT:water ratio of 6:1 (mg:g), prepared according to Example 1, is spin-coated on a silicon wafer substrate at 500 rpm for 30 sec. Water evaporates from the dispersion, and the CNT forms into a coating film on the substrate, with a thickness of about 0.5 µm.

Example 7

Coherent SWCNT Coating Films on Substrates (Dip-Coated)

Approximately 1 liter of the aqueous CNT dispersion with CNT:water ratio of 6:1 (mg:g), prepared according to Example 1, is placed in a tall rectangular plastic tank (30×12×3 cm). 4×6 inch sheets of copper and aluminum, and a 4-inch diameter silicon wafer are sequentially dipped into the dispersion, and each substrate is withdrawn from the dispersion at a speed of 0.2 cm/s. Water is evaporated from each dipped sample under ambient conditions. The CNT forms into a cohesive coating film on each substrate, with a thickness of about 5 µm.

Example 8

Coherent SWCNT Coating Films on Substrates (Spray-Coated)

The aqueous CNT dispersion prepared according to Example 1 with CNT:water ratio of 6:1 (mg:g), is sprayed on an aluminum foil substrate and the water is evaporated under ambient conditions. The CNT forms into a cohesive coating film on the substrate with a thickness of about 50 µm.

Example 9

Fabrication of Transparent CNT Assemblies

An aqueous CNT dispersion was prepared via the sonication-microfluidization route described in Example 1. The residual dispersions R1, R2, and R3 were collected after microfluidization as described in Example 2. About 5 mL of the R 3 dispersion (the most diluted CNT/water dispersion collected from the microfluidizer) were cast into a 5-cm diameter glass dish. Water was evaporated from the dispersions under ambient conditions without restriction for 3 days.

Figure 9:
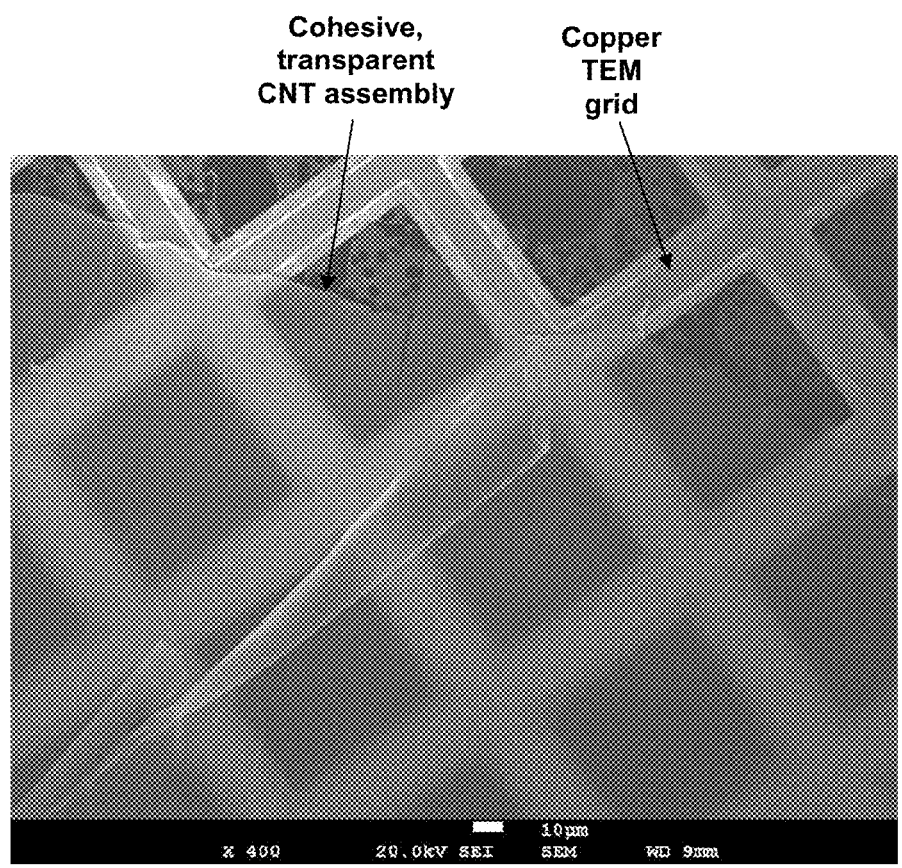
FIG. 9 is an electron microscope image of a cohesive, optically transparent CNT assembly over a TEM copper grid (with the copper grid visible through the CNT assembly, prepared as described in Ex. 9.

After evaporation of the water, the CNT formed into continuous, cohesive, thin wafer segments which were removed from the glass dish as free standing, transparent CNT wafer portions about 1 cm in length. A high resolution electron microscope image of a portion of the transparent cohesive CNT wafer over a TEM copper grid is shown in FIG. 9. The thickness of the transparent CNT assembly was 120 nm.

Example 10

Fabrication of Free Standing CNT Wafer from Aqueous Dispersion Using Sonication Approximately 50 mg of Baytubes® MWCNT (Bayer MaterialScience, Leverkusen, Germany, containing approximately 0.1-0.5 at. % of (—COOH) and/or (—OH) functional groups, was introduced into 25 mL of water in a beaker and processed by probe sonication using 3 cycles of 15 minute duration. The resulting CNT/water dispersion was prepared with approximate ratio of 2:1 (mg/g).

Figure 10:
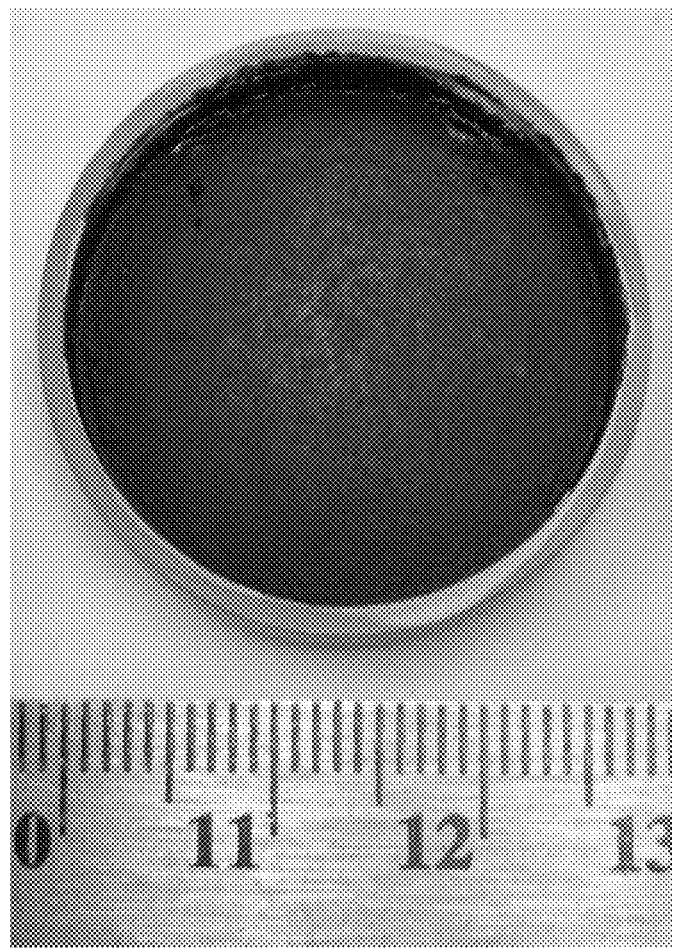
FIG. 10 shows an optical image of an intact, cohesive 3-cm diameter CNT assembly prepared as described in Ex. 10.

About 5 mL of the CNT/water dispersion was cast into a Pyrex dish of 3 cm diameter. Water was evaporated from the dispersion in air at room temperature without covering the dish. After 16 hours, the water was completely evaporated and the CNT formed into an intact and cohesive free standing CNT wafer. FIG. 10 shows the resulting intact, cohesive 3-cm CNT wafer that formed upon removal of the water. The thickness of this wafer was about 10 µm.

Example 11

Fabrication of Adherent CNT Wafer from Aqueous Dispersion Using High Shear Mixing and Sonication Approximately 300 mg of Baytubes® MWCNT were introduced into 200 mL of water in a sealed flask. The CNT/water mixture was dispersed using a high shear mixer (10,000 rpm for 60 min) while simultaneously sonicating in an ultrasonic bath for 60 min. The dispersion was then sonicated for an additional hour at 45° C. using the ultrasonic bath. The resulting CNT/water dispersion was prepared with approximate ratio of 1.5:1 (mg/g).

Figure 11:
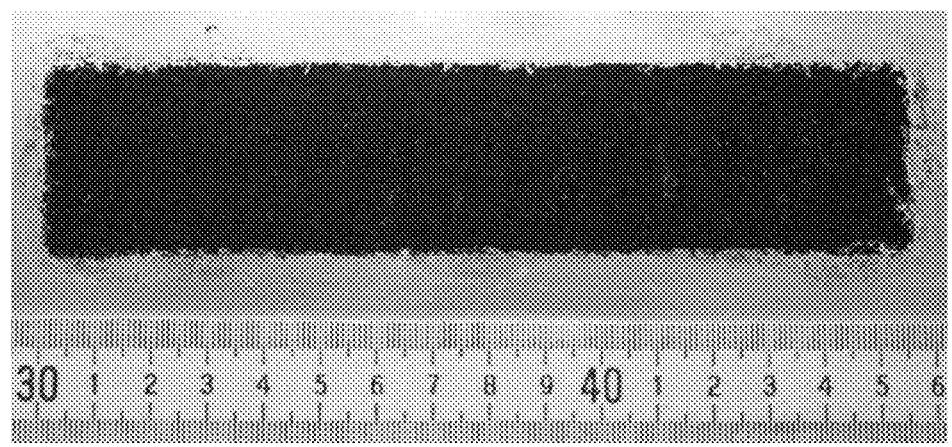
FIG. 11 shows an optical image of a cohesive, adherent CNT assembly on an aluminum foil substrate, prepared as described in Ex. 11.

About 50 mL of the CNT/water dispersion was cast into a silicone rubber retainer of approximate exposure dimensions 15 cm x 3.5 cm placed over aluminum foil (All foils, 25 µm thick). The silicone retainer formed a leak-tight seal with the aluminum foil. Water was evaporated from the dispersion at room temperature and was completely evaporated after 1 day. The CNT formed into an intact assembly which adhered to the aluminum foil (FIG. 11). The thickness of the CNT assembly was about 25 µm.

Example 12

Fabrication of mm-Thick CNT Assembly from Aqueous Dispersion Using Sonication Approximately 120 mg of Baytubes® MWCNT were introduced into 40 mL of water in a beaker and processed by probe sonication using 3 cycles of 15 minute duration. The resulting CNT/water dispersion was prepared with approximate ratio of 3:1 (mg/g).

Figure 12:
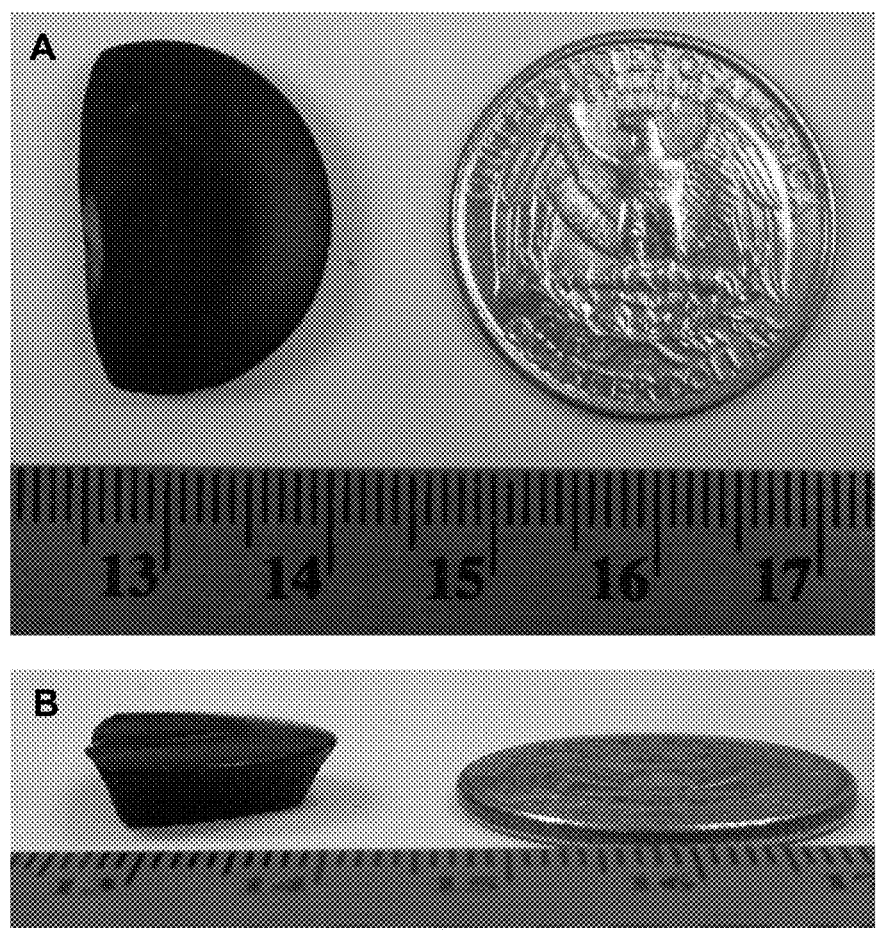
FIG. 12 shows (A) top view, and (B) side view optical images of an intact, cohesive 3-4 mm thick free-standing CNT assembly, prepared as described in Ex. 12.

The CNT/water dispersion (40 mL) was cast into a 50 mL capacity glass beaker and the water was evaporated overnight (or for about 16 hours) in a convection oven at 40° C. The CNT formed into a free-standing cohesive disc-shaped structure as shown in FIG. 12. The cohesive MWCNT disc was about 3-4 mm thick with a mass of about 500 mg. The MWCNT macro-structure possessed a matte top surface and shiny bottom surface.

Example 13

Electrical Resistance and Resistivity of CNT Assemblies

To be useful as a current collector for such devices as a capacitor, fuel cell, or battery, a material needs to have sufficiently low resistivity (on the order of $10^{-2}$ $\Omega$-cm or below) and sufficient mechanical robustness (high tensile strength and resistance to breakage).

To establish that the cohesive assemblies have sufficiently low resistivity to be used as current collectors, assemblies prepared as described in Example 1 were measured for electrical sheet resistance and resistivity as follows:

From each assembly, a sample of rectangular or square geometry was cut with lengths greater than 1 cm on all sides. Each sample was mounted in a sample mount, and two electrical contact pairs (two current carrying and two voltage sensing) were directly compressed to the sample, in a standard Kelvin-type (4-point) probe configuration. The sample was positioned such that the four metal tips of the four-point probe made direct contact with the sample without puncturing through it.

A constant current of 1 mA was made to flow the length of the sample by using a high impedance current source. The voltage drop across the sample was measured using a high impedance digital voltmeter. The surface (sheet) resistance, $R_s$ in $\Omega$ (or $\Omega$/sq), of the sample was determined from the ratio of the stable voltage registering on the voltmeter, V, to the value of the output current of the current source, I, multiplied by the geometric factor $\pi/\ln 2 \approx 4.53$:

$$R_s = 4.53(V/I).$$

The thickness (t) of each sample was measured using a profilometer, digital micrometer, or scanning electron microscope, and the electrical resistivity $\rho$ of each sample in $\Omega$-cm, was then calculated using the formula:

$$\rho = R_s(t)$$

Sheet resistances of SWCNT assemblies prepared according to Example 1 were between 27 and 41$\Omega$ per square. Resistivities of cohesive carbon assemblies prepared according to Example 1 were between about 0.06 and 0.22 $\Omega$-cm.

Resistivities of some of the SWCNT assemblies were sufficiently low such that they could be utilized as current collectors in electronic storage devices such as capacitors, fuel cells, or batteries. Moreover, cohesive assemblies fabricated per the present invention possess the necessary mechanical properties to be used as current collectors, replacing current collectors made from metals such as aluminum or copper. This is in direct contrast to other types of carbon assemblies, including, for example, activated carbon, and other CNT-based assemblies such as those made from CNT forests, which do not possess the necessary robustness to be used as current collectors in place of metal plates.

Example 14

Capacitor Electrode Comprising a Cohesive Assembly of SWCNT

Cohesive carbon assemblies are prepared following the procedure described in Example 2. The SWCNT assemblies are about 9 cm in diameter and about 20-35 µm thick (measured using a profilometer, model Dektak 150, Veeco Instruments Inc., Plainview, N.Y.). Discs about 0.625 inch in diameter are cut from the assemblies using a standard laboratory blade.

Some of the discs are placed in a sealed quartz tube inside a furnace at room temperature (about 20° C.). The tube is purged for one hour by flowing helium through it at 20 sccm. The discs are then heated in the furnace at 10° C/minute to 1000° C. while continuing the flow of helium. While holding the temperature at 1000° C., helium flow is stopped, and a mixture of 5% chlorine and 95% argon gas is introduced at 20 sccm. These conditions are maintained for 1 hour, then the gas is switched back to helium at 20 sccm for 30 minutes. The gas is then changed to a mixture of 5% hydrogen and 95% argon at 20 sccm for 30 minutes to remove residual chlorine. Then, the gas is switched back to 20 sccm helium and maintained for 2 hours. The furnace is then cooled naturally to room temperature.

The discs treated with chlorine as above, and some non-treated discs, are then dried under vacuum at 195° C. for 12 hours immediately prior to further use.

For comparison with the SWCNT discs, Activated Carbon (AC) with the product name Norit DLC Super 30 is obtained from Norit Nederland BV (Amersfoort, The Netherlands). A disc-shaped piece about 0.625 inch in diameter and between 40 and 60 μm thick is formed from the AC powder using standard manufacturing methods. The AC disc is dried at 60° C. for 1 hour immediately prior to further use.

Electrochemical double-layer capacitor (EDLC) cells are fabricated using the SWCNT and AC discs. Prototype cells are assembled in a dry box using metal plates clamped against each electrode face as current collectors. The cells are tested for their properties and performance as electrodes in symmetric electrochemical capacitors rated at 2.0 volts, using 1.0M tetraethylammonium tetrafluoroborate (TEATFB) salt in propylene carbonate as the electrolyte.

Test capacitor cells are conditioned by holding them at 2.0 V for ten minutes, then charge/discharge cycled using a battery/capacitor tester (Model BT2000, Arbin Instruments, College Station, Tex.) thirty times between 1.0 and 2.0 V using 2.5 mA current. Then, electrical performance measurements are made in the following order:

1. Leakage current after 30 minutes at 1.0, 1.5, and 2.0 V
2. EIS (electrochemical impedance spectroscopy) measurements at 2.0 V bias voltage
3. Constant-current and constant-power charge/discharge measurements using the Arbin tester Representative results of the above measurements are summarized in Table 1.

Equivalent series resistances (ESR) of all cells were comparable.

The 30 minute leakage current of cells fabricated with electrodes made from both non-treated and $Cl_2$-treated SWCNT assemblies is superior (i.e. lower) compared to that of the cell fabricated with AC electrodes. Chlorine-treated SWCNT cells show slightly better leakage current compared to non-$Cl_2$-treated cells, but the difference might be statistically insignificant. The much lower leakage current of the SWCNT cells suggests that they may be operated at substantially higher voltages compared to AC-based cells.

The SWCNT cells exhibit very high discharge rate, with full capacitance discharge times on the order of about 0.3-0.4 seconds, or less, which is retained up to 5 A/g current, compared to about 2-3 seconds for the AC cell. Furthermore, the AC cell does not retain full capacitance to this same current level. This indicates that the SWCNT cells show superior power performance compared to the AC cell.

Power density of the SWCNT cells is estimated to be at least 100 kW/kg. This is superior to the power density of typical commercial AC-based EDLCs, which is about 10 kW/kg or less, and is at least equivalent to the power performance of any currently available commercial EDLC.

Due to limitations within the test, absolute full capacitance discharge time and power density of the SWCNT cells can not be determined. For these two parameters, the SWCNT cells show power performance in excess of the measurement capability of the test equipment.

Another strong indicator of pulse power performance of a capacitor device is the frequency at which the complex impedance phase angle reaches 45°. A higher frequency indicates better performance. Capacitors fabricated from SWCNT electrodes show 45° phase angle frequency of about 2.4 Hz, whereas the capacitor based on AC shows 45° phase angle frequency of 0.5 Hz. For this performance metric, $Cl_2$-treated and non-treated SWCNT cells perform similarly.

Overall, SWCNT electrodes of the present invention out-perform commercial activated carbon currently used as the standard electrode material in EDLC devices, in terms of pulse power performance.

TABLE 1

Performance of Capacitor Cells Utilizing SWCNT Electrodes of the Present Invention, Compared to Activated Carbon Electrode.

| Cell ID and Type | ESR (Ω) | 30 minute leakage current (μA) | | | Discharge Time (sec) | Power Density (kW/kg) | EIS Frequency for 45° phase angle (Hz) |
| --- | --- | --- | --- | --- | --- | --- | --- |
| | | 1.0 V | 1.5 V | 2.0 V | | | |
| No $Cl_2$ | 0.64 | 1.6 | 2.4 | 5.0 | 0.3-0.4* | >100 # | 2.4 |
| $Cl_2$ treated | 0.50 | 0.7 | 1.4 | 3.8 | | | 2.4 |
| AC | 0.54 | 3.9 | 7.3 | 33.1 | ~2-3 | ~10 | 0.4-0.5 |

*Minimum measurable full capacitance discharge time under the test conditions; actual time is lower.
Maximum measurable power density under the test conditions; actual power density is higher.

Example 15

Battery Electrode Comprising a Cohesive Assembly of SWCNT

A cohesive carbon assembly is prepared following the procedure described in Example 2. The SWCNT assembly is about 9 cm in diameter and about 25-35 μm thick.

A section of appropriate size and shape is cut from the assembly and tested for its performance as an anode in a lithium-ion battery, using the method described by Y. NuLi in *Materials Letters* 62 (2008) 2092-2095.

The test method consists of the following essential steps: (1) the cohesive SWCNT assembly is installed in a test battery cell, (2) the cell is discharged, and (3) the power and energy densities from the discharge curves are measured.

Then, the data for the cell with the SWCNT anode is compared with the same data obtained from a sampling of similar cells having other types of anode materials. The performance of the SWCNT assembly-based lithium-ion battery anode is thereby compared to the performance of lithium-ion battery anodes composed of other materials such as graphite, hard carbon (i.e. diamond-like carbon), titanate, silicon, germanium, other CNT-based electrodes that require binder or structural support, and the like.

Example 16

Fuel Cell Electrode Comprising a Cohesive Assembly of SWCNT

A cohesive carbon assembly is prepared following the procedure described in Example 2. The SWCNT assembly is about 9 cm in diameter and about 25-35 µm thick (measured by profilometer).

A piece of the SWCNT assembly is analyzed by nitrogen adsorption/desorption using a model TriStar 3000 equipment manufactured by Micromeritics Instrument Corp., Norcross, Ga. The assembly has a BET surface area of 1680 $m^2/g$, and a total desorption pore volume of 1.75 $cm^3/g$. The density of the assembly is determined to be about 0.5 $g/cm^3$ by dimensional and weight measurements. The porosity of the assembly is thereby calculated as about 88%.

A section of appropriate size and shape is cut from the assembly and the section is then coated with platinum metal particles according to a method described in US Patent Application Publication US 2009/0015984A1.

The Pt-coated section of SWCNT assembly is evaluated for its performance as a fuel cell electrode, using the method described by B. Fang et al, *Electrochemistry Communications* 11 (2009) 1139-1141. The cell voltage and power density vs. current density behavior of the fuel cell containing the SWCNT assembly-based electrode, is then compared to the performance of standard fuel cells containing carbon black, carbon paper, and/or carbon cloth-based electrodes, and to the performance of fuel cells containing other potential alternative electrode materials.

Although several embodiments of the invention have been described in the Examples given above, those of ordinary skill in the art will appreciate that various modifications can be made without departing from the scope of the invention. Accordingly, other embodiments are within the scope of the following claims.

What is claimed:

1. An article comprising a substrate and a cohesive carbon assembly coated onto at least one surface of the substrate, wherein the cohesive carbon assembly is a self-assembled monolithic structure having uniformly distributed carbon, the cohesive assembly has a distinct shape and size, the cohesive assembly is free-standing, the cohesive assembly does not require mechanical support by other material or require a binder material, and is prepared by a method comprising the steps of:
   a. obtaining a functionalized carbon starting material in a form of powder, particles, flakes, loose agglomerates, aqueous wet cake, or aqueous slurry; said functionalized carbon starting material is a carbon starting material which has been covalently or non-covalently functionalized such that it is dispersible in water;
   b. dispersing the functionalized carbon starting material in an aqueous solution in a prescribed ratio to form a dispersion;
   c. removing greater than 99% of liquid from the dispersion in a controlled manner, and
   d. forming the cohesive carbon assembly without applying mechanical forces to the carbon.

2. The article of claim 1, wherein the functionalized carbon starting material is selected from the group consisting of carbon nanotubes, graphene, graphene oxide, graphite, expanded graphite, exfoliated graphite, amorphous carbon, activated carbon, and any combinations thereof.

3. The article of claim 2, wherein the functionalized carbon starting material contains acyl chloride, carboxyl, hydroxyl, amide, glycerol, organic ester, PEO, PEG, PVA, amino terminated polystyrene, BSA, PABS, or any combination thereof.

4. The article of claim 2, wherein the functionalized carbon starting material is carbon nanotubes.

5. The article of claim 4, wherein the functionalized carbon nanotubes are single-walled carbon nanotubes, double-walled carbon nanotubes, multi-walled carbon nanotubes, or any combination thereof.

6. The article of claim 1, wherein the aqueous solution is de-ionized water, distilled water, purified water, or any combination thereof.

7. The article of claim 1, wherein step b further comprises dispersing the carbon starting material in water in the presence of mechanical agitation.

8. The article of claim 7, wherein the mechanical agitation comprises sonication, mechanical stirring, high shear mixing, microfluidization, homogenization, or any combination thereof.

9. The article of claim 1, wherein the functionalized carbon starting material is functionalized single-walled carbon nanotubes, the water is purified or de-ionized water, and the ratio of carbon starting material and water is between about 0.1 and about 20 mg carbon per gram of water.

10. The article of claim 1, wherein the functionalized carbon starting material is dispersed in the aqueous solution that is substantially free of a binding material.

11. The article of claim 1, wherein the method further comprises applying the dispersion to a hydrophobic surface after step b and before step c.

12. The article of claim 11, wherein the hydrophobic surface comprises a dimethyl organosilane, a fluorinated dimethyl organosilane, a fluorinated polymer or Teflon.

13. The article of claim 1, wherein the method further comprises applying the dispersion to a hydrophilic surface after step b and before step c.

14. The article of claim 13, wherein the hydrophilic surface is selected from the group consisting of metal surface, glass surface, silicon surface, plastic surface, ceramic surface, and any combination thereof.

15. The article of claim 14, wherein the metal is selected from the group consisting of aluminum, copper, gold, silver, platinum, tantalum, titanium, stainless steel, and any combination thereof.

16. The article of claim 1, wherein the cohesive carbon assembly is an electrode in a capacitor, a fuel cell, a battery, or an energy storage device.

17. The article of claim 1, wherein the cohesive carbon assembly has a thickness of about 0.02 µm to about 2,000 µm.

18. The article of claim 1, wherein the cohesive carbon assembly has an electrical resistivity of less than about 0.2 Ω-cm.

19. The article of claim 1, wherein the cohesive carbon assembly has an electrical sheet resistance of less than about 50 Ω per square.

20. The article of claim 1, wherein the cohesive carbon assembly is transparent.

21. The article of claim 1, wherein the functionalized carbon starting material is dispersed in the aqueous solution that is substantially free of a surfactant.

22. The article of claim 1, wherein the cohesive carbon assembly is a self-assembled monolithic structure consisting of uniformly distributed carbon.

* * * * *